(12) United States Patent
Kragh

(10) Patent No.: US 9,805,213 B1
(45) Date of Patent: *Oct. 31, 2017

(54) IDENTITY VALIDATION AND VERIFICATION SYSTEM AND ASSOCIATED METHODS

(71) Applicant: James F. Kragh, Winter Park, FL (US)

(72) Inventor: James F. Kragh, Winter Park, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/047,926

(22) Filed: Feb. 19, 2016

Related U.S. Application Data

(63) Continuation-in-part of application No. 14/613,115, filed on Feb. 3, 2015, now Pat. No. 9,280,684, which is a continuation-in-part of application No. 13/898,669, filed on May 21, 2013, now Pat. No. 8,984,282, which is a continuation-in-part of application No. 12/792,980, filed on Jun. 3, 2010, now Pat. No. 8,464,046.

(60) Provisional application No. 61/183,600, filed on Jun. 3, 2009.

(51) Int. Cl.
*G06F 21/00* (2013.01)
*G06F 21/62* (2013.01)
*G06F 17/30* (2006.01)

(52) U.S. Cl.
CPC .... *G06F 21/6227* (2013.01); *G06F 17/30312* (2013.01); *G06F 17/30424* (2013.01)

(58) Field of Classification Search
USPC ........................................................ 713/156
See application file for complete search history.

(56) References Cited

U.S. PATENT DOCUMENTS

| | | |
|---|---|---|
| 6,892,679 B2 | 5/2005 | Jameel et al. |
| 7,047,204 B1 | 5/2006 | Wood et al. |
| 7,078,647 B2 | 7/2006 | Kou et al. |
| 7,239,285 B2 | 7/2007 | Cook |
| 7,280,988 B2 | 10/2007 | Helsper et al. |

(Continued)

OTHER PUBLICATIONS

"Information Aggregation and Group Decisions", Sobel, University of California, San Diego; Jan. 17, 2006; Journal of Economics Literature.

*Primary Examiner* — Jason Lee
(74) *Attorney, Agent, or Firm* — Carl M. Napolitano; GrayRobinson, P.A.

(57) ABSTRACT

A system and method verify and validate user identity for enrollment in a secure personal dataset accessing system, wherein a personal dataset includes identifiable attributes of a user. Authenticity of an asserted user identity includes electronically verified identifiable attributes to form the personal dataset. A biometric identifier is automatically captured for validating the identifiable attributes by confirming that the asserted identity matches identifiable attributes. A traceable e-audit trail is provided in an enterprise infrastructure and bench mark performance indicator. A generated digital security element results in the user electronically receiving a password and unique electronic address assigned to the user. The digital security element is then transmitted to the user and enables electronic access to the personal dataset, the personal dataset having been authenticated through the verification and validation. The user may use a smartphone, tablet, PC or laptop to generate their Emergency Medical and Contact DataSet.

1 Claim, 21 Drawing Sheets

(56) References Cited

U.S. PATENT DOCUMENTS

| | | |
|---|---|---|
| 7,424,437 B2 | 9/2008 | Maus et al. |
| 7,668,734 B2 | 2/2010 | Pugh |
| 7,742,982 B2 | 6/2010 | Chaudhuri et al. |
| 2006/0206724 A1 | 9/2006 | Schaufele et al. |
| 2007/0061169 A1* | 3/2007 | Lorsch ............... G06F 19/322 705/3 |
| 2007/0075135 A1 | 4/2007 | Dettinger et al. |
| 2008/0109370 A1 | 5/2008 | Moshir et al. |

* cited by examiner

FIG. 6

PVID Privacy Class Matrix

| Privacy Levels | Class Name | Temporary | Test | General | Psychiatry | Cancer | HIV | Research | Genetics | Organ Registry | Transplant History | Employer | HIE Participation | Authorizations | Privacy Security Access/Class Definitions |
|---|---|---|---|---|---|---|---|---|---|---|---|---|---|---|---|
| Share all Data | | | | | | | | | | | | | | | |
| Restricted data sharing | | | | | | | | | | | | | | | |
| Sharing with restricted access | | | | | | | | | | | | | | | |
| No sharing of data | | | | | | | | | | | | | | | |
| Emergency Only | | | | | | | | | | | | | | | |
| Consents | | | | | | | | | | | | | | | |
| Preferences Authorizations | | | | | | | | | | | | | | | |
| Directives DNR, organ donation | | | | | | | | | | | | | | | |
| Opt-in - Opt-out | | | | | | | | | | | | | | | |
| Medical - Power of Attorney | | | | | | | | | | | | | | | |

| ATTRIBUTE GROUPS | | A | B | C | D | E | F | G |
|---|---|---|---|---|---|---|---|---|
| | | Legal Name with limited demographic data | Opt-Out: No data sharing except column-ef A1 | Share Emergency Medical & Contact Data | Opt-in share my PHI with Medical Network | Understand PHI will be e-encrypted as shared via HIEs | Will use the following devices to create-share-receive PHI | Attribute aggregation function |
| FUNCTION | | | | | | | | |
| Consent | 1 | Y (default) | Y N | Y N | Y N | Y N | Personal Computer | I understand attributes can be bundled to enhance efficiencies in sharing and distributing my Protected Health Information |
| | 2 | | | | | | Tablet | |
| | 3 | | | Break the Glass | | | iPad | |
| Understand | 4 | | | Y N | | | SmartPhone | |
| | 5 | | | | | | cell phone | ☐ I agree |
| Restricted Data Sharing | 6 | | | Y N | Y N | | medical device(s) | |
| | 7 | | | | | | other mobile devices | |
| Restricted Access | 8 | | | Y N | Y N | | I consent that the selected device(s) will be used by me in managing my health activities or by an entrusted 3rd party with a digital ID and LoA equal to or greater than mine. | |
| | 9 | | | | | | | |
| Sharing with Restricted Access | 10 | | | | Y N | | | |
| | 11 | | | | | | | |
| | 12 | | | | | | | |
| | 13 | | | | | | | |
| | 14 | | | | | | | |
| | 15 | | | | | | | |
| | 16 | | | | | | | |
| Consent | 17 | | | | | | Y N | |

My PHI DATA Segmented e-records

Actors / Subjects

Columns (A–Ah):
- A: Hospitals ACO's PCMHs
- B: Home healthcare
- C: Rehab Centers
- D: PHI Analytics
- E: Nursing HOMES
- F: Genetics
- G: HIV
- H: STD
- I: Cancer
- J: Psychiatry
- K: Research
- L: e-Health Record
- M: Private medical tests
- N: Juvenile Abuse - 23yr issues
- O: Workmans Comp
- P: HR Department
- Q: Workplace
- R: Profile change
- S: Attribute Change
- T: Authentication Change
- U: Chid/dependent health records
- V: Clinical value sets
- W: Chronic Disease event records
- X: e-Audit Trails
- Y: Care plan Mgt
- Z: My Health Data Repository
- Ab: Date - Time clock
- Ac: New VHID#
- Ad: Dates, gene Egg, tissue, Sperm, Blood, etc.
- Ae: Anonymous VHID#
- Af: Temporary VHID#
- Ag: End of Life Care
- Ah: Mobile Medical Device Images PHI Errors and Recovery Rows (1–21): Res and Professional Approved & Authenticated with Digital ID LoA 3cr 1. Self-My PHI
2. Family Friend
3. Caregiver Gardian
4. Physician General ~ Specialist
5. Caregiver Gardian
6. Nurses EMT
7. Pharmacist
8. Radiology Therapist
9. Psychologist Psychotherapist
10. Health Coach Health Advocate
11. Financial Rep Claims data rep
12. Principal Investigator Auditor
13. 3rd Part Claims Rep Risk Analysis Professional
14. Agent Trustee Power of Attorney Medical
15. Chronic Disease Specialist
16. Health Educator
17. Spiritual Representative Anonymous Trustee
18. Workmans Comp
19. My VHID # Stolen, Compromised, or Breached. Need new VHID#
20. Create a Temporary VHID #
21. Create an Anonymous VHID #
22. Patient and Provider errors

FIG. 7A    Core User Authenticated Identity Attributes that can be shared with a Relying Party - RP (User Attribute Metric Values documented during the Verification, Validation and Registration Process; time date stamped for credential binding and serialization tracking)v4

| | A | B | C | D | D | E | F | G | H |
|---|---|---|---|---|---|---|---|---|---|
| Authoritative Gov Agencies or via 3rd Party Contractor LOC = Level of Confidence with a being the top Metric value | United States Postal System Name; Address verification | Social Security Administration SSN#, Name and Date of Birth verification | Federal Communication Commission Home- cell phone # with address verification | Department of Transportation - State DMV Drivers license verification | Federal Reserve System Credit Bureaus, credit-debit card, bank account verification | Depart of State passport verification, 3rd party-Business ID professional credentials | Depart of Defence + Govt issued ID's cards Validated user credentials passports given cards | State, Regional or Local Utility Monthly Utility Bill to verify address | A Local Government issued identity type cards for unemployed and undocumented |
| LOC 8 Trust Marks: a certified, contractual relationship with a Trust Framework. Metric value 8 | | | | | | | | | |
| LOC 7 Authoratative data with 3rd Party or Notarized document  Metric value 7 | | | | | | | | | |
| LOC 6 A combination of Authoratative, Aggregated and Direct Data w 3rd party verified ID  Metric value 6 | | | | | | | | | |
| LOC 5 Aggregated and Direct data capture with some Authorative + Social ID Metric value 5 | | | | | | | | | |
| LOC 4 Derived and Direct data capture with Social ID Metric value 4 | | | | | | | | | |
| LOC 3 Derived and Self Asserted data Metric value 3 | | | | | | | | | |
| LOC 2 Derived and Self Asserted data Metric value 2 | | | | | | | | | |
| LOC 1 Derived with un-verified user input  Metric value 0 | | | | | | | | | |

FIG. 7B   Biometrics, Devices and other Attribute Value rankings linked to an Authenticed Identity (User Attribute Metric Values documented during the Verification, Validation and Registration Process; time date stamped-basis for serial binding Prime-Device w Digital ID and Biometrics)

| | 1 | 2 | 3 | 4 | 5 | 6 | 7 | 8 | 9 |
|---|---|---|---|---|---|---|---|---|---|
| Offerings by Companies or by 3rd Party Contractors. BC Value = Biometric credential Strength; 8 is the top Metric value; 8 represents biometric group. | Knoledge-Based Authentication National Contractor with Government Pass-Fail | Out-of-Band Call captures digital voice print, phone # national contractor to banks | Biometric types with NIST's Supporting Guidelines for Finger, Hand, Face, Iris, Voice | Telco Registered Smartphone as User's Primary Mobile ID Credentialed Device & Hub | Smart Cards and Tokens used for with multi-factor Authentication + Bar & QR Codes Images Pictures | Financial Institutions BMV Credit-Debit as Authenticator Cards e-Driver's License Valid | Tablets, laptops, PCs, appliances apps, devices & sensors linked to user's Primary Hub #4 | Biometrics: All forms of body motions and sounds: tounge, blinking, nose, humming, etc. | Biometrics: Internal body activity: brain waves, heartbeat, veins, smell, soundwaves, etc. |
| BCS8 Trust Marks, a certified, contractual relationship with a Trust framework. Value-8 | | | | | | | | Catagories 8 & 9 are currently being analyzed in the NIST Lab | Catagories 8 & 9 are currently being analyzed in the NIST Lab |
| BCS7 Notarized document, sealed verified-encrypted Token, encrypted Biometric, TPM back keys, Unique Device ID. Value-7 | | | | | | | | | |
| BCS6: BCS5 plus multifactor authentication using User-Hub with OTP, Trusted Tokens or Biometrics or a Notary on-line system. Value-6 | | | | | | | | | |
| BCS5 1, 2, 3 with known device sensors via a trusted Hub enrollment process 4, OTP system. Value-5 | | | | | | | | | |
| BCS4 Derived Direct data capture KIBA, OTP, Cell or Smartphone #4, Social Id and Shared Secret. Value-4 | | | | | | | | | |
| BCS3 KBA, Derived and Self Asserted data, user name, password, OTP, cell phone registration #4. Value-3 | | | | | | | | | |
| BCS2 KBA, Derived Self Asserted data or Local Municipal Gov ID Card #H in FIG. 7A Value-2 | | | | | | | | | |
| BCS1 User data self asserted un-verifable user is pseudonymous. Value-0 | | | | | | | | | |

FIG. 7C  Registry Attribute Coded Values that support a user's Authenticated Identity for Relying Parties (User Attribute Trust Levels- Values documented during Verification, Validation& Registration Process; time date stamped-basis for Digital ID binding, serialization and trackings)

| | 1 | 2 | 3 | 4 | 5 | 6 | 7 | 8 |
|---|---|---|---|---|---|---|---|---|
| User Attribute Codes for sharing with Relying Parties | Gender<br>G.1-Female<br>G.2-Male<br>G.3-Other | Consent Access<br>C.1-General<br>C.2-Conditional<br>C.3-Time Sensitive<br>C.4-Real Only<br>C.5-User defined Access<br>C.6-No Consent | RP Directive<br>R.1-Don't Share Data<br>R.2-Share Data<br>R.3-Share Data 1 Time<br>R.4-No Data Collection or data Aggregation | Tracking<br>T.1-Do Not Track<br>T.2-OK to Track<br>T.3-Restricted Tracking to User Defined Events | Data Refresh-Rate<br>DR.1-Annually<br>DR.2-Quarterly<br>DR.3-Monthly<br>DR.4-Real Time | Privacy Consent Directives<br>PC.1-Grant Authorization<br>PC.2-Withhold Authorization for<br>PC.3-User data for specific use<br>PC.4-User data that can be used and or disclosed | Prim-Hub FIG. 7B-<br>4-Qualified MFA Authenticators<br>7B.1.0<br>7B.2.0<br>7B.3.0<br>7B.5.0<br>7B.7.0<br>7B.9.0 | Future User Directives |
| TRUST | | | | | | | | |
| Level-4 | LOC-V.8<br>LOC-V.7 | | BCS-V.8<br>BCS-V.7 | Levels of Trust that represent a User from FIG. 7A and FIG. 7B | | | | |
| TRUST | | | | | | | | |
| Level-3 | LOC-V.6<br>LOC-V.5 | | BCS-V.6<br>BCS-V.5 | | | | MFAs 7B: 1.0;<br>2.0; 3.0; 5.0; 6.0; 7.0 | |
| TRUST | | | | | | | | |
| Level-2 | LOC-V.4<br>LOC-V.3 | | BCS-V.4<br>BCS-V.3 | | | | | |
| TRUST | | | | | | | | |
| Level-1 | LOC-V.2<br>LOC-V.1 | | BCS-V.2<br>BCS-V.1 | | | | | |

LOC-V.# = Levels of Confidence Value for Authenticated Attributes

BCS-V.# = Biometric-Credential Strength Value of Attribute Strength

EXAMPLE OF METADATA SET SENT TO A RELYING PARTY:  JK, FL 32794, 1963, TL-3, LOC-V.6, BCS-V.5, G.2, C.1, T.1

All Attribute Metadata, Metadata sets and related values are stored in the Attribute Registry

Emergency Medical Data Set* for

Name: Octivia Helios  Gender: Female  EMPI: NA
Authenticated* Primary HIE/RHIO: Orlando, FL FLCF32802-115
Confidential

Personal Data - Contact Information

DOB: January 22, 1945
Race/Ethnicity: Hispanic American
Primary Language: Spanish
Home Address: 123 Bastile Dr. Apt. 3
Boston, MA 02102
Phone number: home 999-999-9999
                 cell: 111 111-1111

Emergency Contact Data:
Physician contacts:
Dr. Thomas E. Duitrite - Primary Care
office # 999-999-9999
Dr. Julie P. Quantos OBGYN
office # 999-999-9999
Family/Friend contacts:
Hector Helios Husband 111-111-1111
Juanita Rodrigus Friend 111-111-1111

Dependent family members under 18:
   Juan Hulios-son 17 - chronic;
   Sally Helios-daughter - 15 w/disability
   Billy Ann Helios-son - 9
   Juanita Helios-daughter - 3

Local ER or Trauma Center:
Name Santa Clara General Hospital
Phone# 888-888-8888

Driver License # 7221-449-331AX
State: Florida
Vehicles registered in: Georgia
Vehicle #1 License Plate # 887 AB7A
VIN # A227 9999 3333 2222 - ACA
Vehicle #2 License Plate # 257 476B
VIN # TRC3 7777 9999 8888 1111

Insurance Coverage:
Blue Cross Blue Shield of California
Plan Name: Options for Good Blue Health
Policy# XRGH12131456577
Group# BA11398
Contact# 1-877 999-1234

*Individual voluntarily consented to an Opt-in
Preference to share this Emergency Medical Data
generated from their Personal Health Record on
04/25/2009  11:11PM PDT

Emergency Medical Data

BLOOD TYPE: AB+

ALLERGIES: as of 12/03/2009
Latex - severe
Sulfa - severe
Peanuts - mild
Feline Dander -moderate

PROBLEM LIST as of 3/11/2009
Hemoptysis,
Mitral Valve Replacement,
Congenital Subaortic Membrane,
Chronic Atrial Fibrillation,
Diabetes Mellitus Type 2,
Stroke without residual deficit,
Congestive Heart Failure, Sciatia

Active MEDICATIONS as of 3/11/2009
Spironolactone (Aldactone),
Amoxicillin (Amoxicillin),
Warfarin (Coumadin),
Digoxin (Digitek),
Valsartan (Diovan),
Ferous gluconate (Ferrous Gluconate),
GlyBURIDE (GlyBURIDE),
Furosemide (Lasix),
Metformin (Metformin Hydrochloride),
Acetaminophenhydrocodone (Vicodin)

ADVANCE DIRECTIVES as of 4/25/2009
DNR and Living Will on file at Attorney's office
Medical Surrogate is named Hector Helios
Organ donation directive on file at State james amigo    Digitally signed by james amigo
               DN: cn=james amigo, o=TNT,
               ou=223, email=goto@home, c=US
               Date: 2010.02.01 07:53:17-05'00'

Confidential - Emergency Medical Data and Contact Information - Confidential
Copyright Good Health Network, Inc. 2009

FIG. 8

IDENTITY VALIDATION AND VERIFICATION SYSTEM AND ASSOCIATED METHODS

CROSS-REFERENCE TO RELATED APPLICATIONS

This application is a Continuation-In-Part application of U.S. Utility application Ser. No. 14/613,115 filed Feb. 3, 2015 and issuing as U.S. Pat. No. 9,280,684, which itself is a Continuation-In-Part of U.S. Utility application Ser. No. 13/898,669, filed May 21, 2013 and issuing as U.S. Pat. No. 8,984,282, which itself is a Continuation-In-Part of U.S. Utility application Ser. No. 12/792,980, filed Jun. 3, 2010, and issuing as U.S. Pat. No. 8,464,046, which itself claims priority to Provisional Patent Application Ser. No. 61/183,600, filed Jun. 3, 2009, the disclosures of which are herein incorporated by reference in their entirety, and all commonly owned.

FIELD OF THE INVENTION

The present invention relates to secure data access systems, and more particularly, to such data access systems that operate under emergency conditions such as needed in medical service environments.

BACKGROUND

The Health Insurance Portability and Accountability Act of 1996 (HIPAA), the fundamental privacy principles of both the Data Protection Act and the Human Rights Act 1998, and the American Recovery and Reinvestment Act (ARRA) in February 2009 followed by April rulings by the Federal Trade Commission (FTC) included a standard of privacy regarding an individual's right to privacy regarding health care data. In January 2013, a new revision of HIPAA 1996, labeled the HIPAA omnibus rule, was issued with increased emphasis on privacy, disclosure of identifiable information and tougher security provisions which comes under the 2009 HITECH Act and the Genetic Information Nondiscrimination act. Under the provisions of HIPAA, ARRA, and the FTC, health information, with few exceptions, can only be shared with the express permission, advance consent, and authorization of the patient (or the patient's legal guardian, as appropriate), and when compromised, electronic notifications must be sent, and followed up with electronic audits and risk analysis.

By way of example, if a patient is unconscious and has provided advance authorization and consent for a licensed health care provider to securely access and view health-related and protected health information with family, next-of-kin, friends, or others involved, the patient's care and emergency care can be shared when in the best interest of the patient.

In Florida, vehicle owners can securely store emergency contact information electronically, including the name and telephone number of at least one person, and link same to their driver's licenses (DL). A law enforcement officer or first responder, if they can locate a driver's license at an accident scene, can contact the Department of Motor Vehicles to obtain emergency contact (ER-Cont.) data. If not available and the vehicle occupants are unconscious or otherwise unable to communicate, notifying the family can be a challenge. ER-Cont. information is only available to police at a crash scene in the state of Florida.

NLETS, the National Law Enforcement Telecommunications System, can interface with Department of Motor Vehicle sites across the country and obtain emergency contact information, but only if linked to a vehicle's vehicle identification number (VIN) and with the driver's consent. However, medical data cannot be collected, stored, accessed, or shared via NLETS, which can cause a loss of critical time gaining access to critical healthcare data, such as allergies, blood type, and other medical data. Such data can save lives or improve the quality of life after a life-threatening event.

As will be addressed throughout this disclosure, attributes contain information about a subject (known also as an actor). A subject's digital ID has a limited number of identity attributes that can be classified as an authenticated attribute such as one's legal name, address, zip-code, age, date-of-birth, or trait features, some of which may be listed on a title or driver's license, that are inherent such as eye color, gender or birth place, by way of example. A subject can also have acquired associated or professional title attributes (lifestyle-celebrity, self-asserted social media name, purchasing behavior, medical or banking activity/profile) which can change easily whereas personal core trait attributes most likely do not change.

Upon being validated and authenticated with a digital ID coupled with authenticated and non-authenticated attributes that have a high trust level of assurance or having public key certificate, in good standing, then a person's (subject) authenticated identity can be enhanced with other attributes that originate from an Attribute Certification, currently recognized as a certified Identity Provider (IdP), that provides an identity proofing process where one's Authentication privilege is created extended to provide "certified binding attributes' that link to a user's primary mobile computing device or 'hub' such as a smartphone or lap top that is user controlled for managing activities such as access control, secure email, access privileges and associated relationships. As a result of the security and auditing process incorporated into Authenticated Attribute Certification there is a strong privilege management policy monitoring effort, risk management process and an attribute/certificate revocation process. Entities, institutions, exchanges, enterprise servers and the environment (defined as 'objects') can also have attributes which are represented by defined and be tagged alpha-numerical characteristics, Bar-QR codes and functions. Authenticated attributes can be used to establish an identity but Attribute certificates (certs) cannot be used to establish an identity but are used to extend the attributes of one's identity. The forgoing is in concert with NIST guidelines.

Anonymization and Pseudonymization are specific de-identification processes that file the intent of HIPAA 1996 and the HIPAA omnibus rules of January 2013. For a user to have Anonymity or Pseudonymity, they first must be known electronically by a trusted third party and have a verified and validated identity. Anonymization is the process that removes the identifying characteristics (HIPAA defined as Protected Identifiable Information (PII) and Protected Health Information (PHI) associated with protected health/clinical information and generates a not so unique health data set. The value of such allows a subject/patient to make a part of or subset of their clinical data (PHI) available for a range of secondary purposes without having to access identifiable clinical information. The same applies to health insurance information that is represented by PII. Such data will be made available on a need to know or on an arranged basis and risk of identity is greatly minimized. The activity is handled through a trusted third party who attests to the validity of the clinical information. Pseudonymization is a specialized class of Anonymization that removes the association and then adds an association between a particular set of data characteristics relating to the data subject in addition to adding more pseudonyms. This is a means by which information can be linked together to the same group of persons over time and across multiple data records without revealing the identity of the person and subject data. A trusted third party play's a critical role if there needs to be a re-identification event that is in response to a major public health event. (Activities defined in HIPAA and HITSP).

As the market place transitions to a digital economy, technical advances in mobile devices like smartphones and laptops that are becoming a user's secure hub for managing their personal network of relationships, applications, devices and sensors that are all connected are opening up new frontiers of convenience, speed and transparency for consumers. Simultaneously, it has also resulted in privacy and security breaches in all markets with healthcare in the lead having over 25% of all patient accounts compromised in 2015. Consumer's, in adopting digital technology, are recognizing they are part of the solution in needing to control and managing their identity, privacy and access to their personal data to guard. They also recognize the beneficial value in using digital tools to enhance their safety and privacy by monitoring personal and related health activities especially during untimely medical events.

There is a need to provide medical help for a patient using a smartphone. By way of example, if the patient is unconscious and has provided advance authorization and consent for a licensed health care provider to securely access and view health-related and protected health information with family, next-of-kin, friends, or others involved, the patient's care and emergency care should be able to be shared when in the best interest of the patient, and in particular during a medical emergency situation where a smartphone provides time access to patient medical information.

Therefore, it would be beneficial to provide a secure system and method for making both VIN and emergency medical data available on an as-needed basis to licensed emergency medical responders, in order that care be provided in a more efficient, safe, and secure fashion if such data can be voluntarily provided and stored in a secure and separate, non-law-enforcement repository, and linked to the NLETS secure infrastructure.

SUMMARY

A system and method are provided for establishing and administering an online secure data sharing network, in particular, for use in emergency situations wherein a patient is unconscious or otherwise unable to communicate. A secure network enables first responders to identify victims, reach next-of-kin, reach their medical doctor, and access emergency medical data at a crash scene or other life-threatening event, the emergency data having previously been authorized for access by the patient.

The secure network may include an emergency medical data registry for each person who elects to participate, by validating, authenticating their identity, and consenting to securely provide emergency medical data on themselves and, if applicable, their children, that the patient has digitally signed. Such emergency medical data can include, for example, blood type, allergies, current medications, surgeries, and emergency medical contact information. The emergency medical data may only be presented in a read-only standards-based format and viewed by a licensed healthcare worker, such as an emergency medical technician (EMT) or emergency department staff member. The data may be owned and controlled by the participant, and may only be modified or deleted by that person. A real-time audit trail is available to the participant, documenting all access events, and a qualified and licensed security professional must be able to access a specific emergency event audit trail for independent auditing purposes without having access to or the ability to view any protected health data.

Embodiments of the invention may comprise a computer implemented system or method to verify and validate a user identity for enrollment in a secure personal dataset accessing system, wherein a personal dataset is electronically received and includes identifiable attributes of the user. Using a computer, authenticity of an asserted identity of the user including the identifiable attributes may be electronically verified and a personal dataset formed. A verified biometric identifier of the user may be automatically captured on the computer for validating the identifiable attributes. The validating may include confirming that the asserted identity matches the identifiable attributes. An e-audit trail is provided having a traceable electronic enterprise infrastructure that is part of the national Trust Framework and bench mark performance indicator.

A digital security element, a generated number as example, may be generated as a result of the verifying, validating and authentication process and results in the user electronically receiving a number or code on user's primary device such as their smartphone, wherein a unique electronic address may also be assigned to the user on that device and bound to the IP address. The digital security element, a one-time number or password/code (OTP) may then be transmitted to the user from the user primary device— smartphone (computer or laptop) and enables secure electronic access to the user's Personal Emergency Medical and Contact Application and Personal Health Record that have been prepopulated with their personal dataset relating to the user, the personal dataset having been authenticated through the verifying and validating steps.

The FCC regulates the telecommunications industry that is the distribution hub for all types of communication devices including smartphone which the FCC recognizes as the defector standard for secure digital internet communication between government agencies and the private sector when incorporating Multi-Factor communication using NIST's identity proofing guidelines. This smart mobile device, having the ability to recognize, when fully verified, validated, authenticated and bound to a user, an individual's previously captured digital biometric(s) that has been validated such as speech, iris, facial, finger-print(s) and other behaviors. This process can allow smartphone device to serve as a personal identifier in unlocking the device while also enabling it to serve as a user's hub.

A step to enhance the security in a secure data exchange may include Multi-Factor communication.

By way of example: Two Factor Authentication. The process described above, where a one-time number/password is shared is referred to as Two-Factor Authentication or Multifactor Authentication. It is a process that uses two pieces, or factors, of previously verified and validated attribute information to verify the identity of a user trying to access (current event) a service or an account. The first factor may include a user's established password and the other factor(s) is commonly used for identity and can include, (if already verified and validated) one or several of the following depending on the event; biometric finger prints, voice prints, retina scans, numeric codes, a unique password, portable tokens some with bar or QR codes, facial scan or a graphic image with pre-defined phrase (something known), PIV, mag-strip-smartcard or a bank issued smart EMV card. Using two or more of these factors together provides a much stronger identity verification process than just a password alone. This process keeps information safe by requiring the user to enter a second layer of security, usually in the form of a generated number, or other factors, before accessing a protected application. Because the second authentication is independent from the username and password, if user's password is stolen, the web application using two-factor authentication is safe from attempted hackers. If at any time a user questions an unusual activity they can add a third form factor. In light of internet activity, the need to enhance privacy and security for consumers and patients, the digital market is converting to Multi-Factor Authentication where 2 or more factors could be used and directly linked to a user's primary mobile hub device such as a smartphone, possibly a laptop.

It is important to note that the same Multi-Factor Authentication process detailed above may be used by the same authenticated user in granting access to their defined or general PII and or PHI based the $3^{rd}$ party's digital credentials. OTP's can be granted by the user for defined pre-approved access times or based on a condition such as a not responding user/patient, an environmental event such a FEMA emergency, a healthcare compliance monitoring schedule, coordinating a plan of care, patient safety issues or a user defined event.

Consider a process that may include: Part 1, One time Password (OTP) where the user provides the password/code: An authenticated user is seeing a medical specialist for the first time and elects to grant permission to the doctor to review the user's medical records for the past twelve months, read only, by providing the Doctor a One-Time-Password (OTP) (Claim 1, P 1-046, Claim 1, lines 26-26): generating a digital security element. Several months later the user plans to take a cross country trip and during the travel time the user wants to provide the companion a functional password for a time-specific period just in case of an untimely event. The Companion should have an equivalent identity, preferably with an equal trust value and both user and companion must execute an authorization consent document.

Part 2 may comprise User Receives a One Time Password (OTP) or code request. In dealing with financial transactions or exchanging confidential information, a sending third party electronic funds transfer entity elects to elevate the security level on a secure transaction and in order for the user to 'access-to-a-transaction', even though the authenticated user is in good standing, the user must respond to a one time password event. The sender notifies the user that he is going to be sending the user an OTP or code within the next minute and the user will have up to 3 minutes to respond or the transaction is suspended. P 282: Claim 1 59-60; column 14/65-67 and 15/1-3. The sender sends the digital security notice and the user responds within the time allotted.

A system and method for adding participants and licensed professionals to a user's network of relationship groupings is an important feature of the teachings of the present invention, and is hereafter further described, by way of example.

Another registry is established for licensed emergency healthcare providers and institutions, so that their credentials, qualifications, and access privileges can be independently verified real time via a third-party source (policy and procedures) and that such validation will enable them to access the emergency medical data registry at local, regional, or national FEMA emergency events. Among the healthcare workers and institutions who may enroll are licensed and credential EMTs, physicians, nurses, hospitals, trauma centers, and ambulance, EVAC and AIRVAC networks, although these are not intended as limitations.

BRIEF DESCRIPTION OF DRAWINGS

Embodiments of the invention are described by way of example with reference to the accompanying drawings in which:

FIG. 6 is an exemplary privacy class matrix, expanded into three relational entity attribute processes;

FIG. 6A illustrates health system infrastructure interfaces (e.g. "objects") such as infrastructure, transport, HIE, HISP, and data capture mobile devices and tools, by way of example;

FIG. 6C illustrates names actor(s)/professional titles that can view defined PHI and shared with whom for a period of time, and a PHI that cannot be viewed, wherein a privacy control matrix is illustrated that designates attributes to a representative such as a medical professional, researcher, administrative specialist for an approved attribute entity, and wherein the designated representative is prequalified (having trusted credentials) to view and access a patient's protected health information as part of the healthcare management team;

FIG. 7A presents a matrix illustrating core user authenticated identity attributes that may be shared with a relying party, by way of non-limiting example;

FIG. 7B presents a matrix illustrating biometrics, devices and other attribute value rankings linked to an authenticated identity, by way of non-limiting example;

FIG. 7C presents registry coded values that may support a user's authenticated identity for relying parties, by way of non-limiting example;

FIG. 8 is an exemplary emergency medical data set according to the teachings of the present invention digitally signed by someone with access to the entire record, by way of example;

DETAILED DESCRIPTION OF EMBODIMENTS

Figure 1:
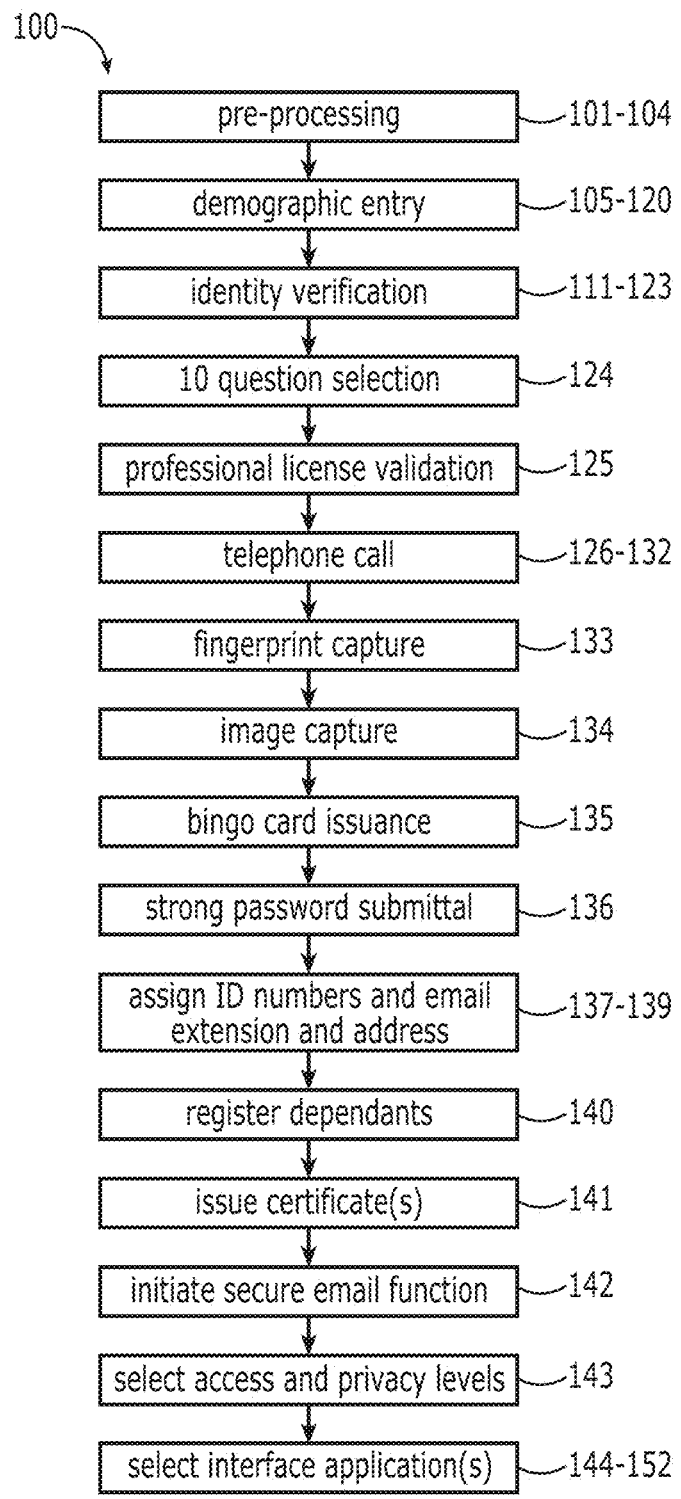
FIG. 1 is a flowchart of one process for identity verification and consent management according to the teachings of the present invention.
Figure 2A:
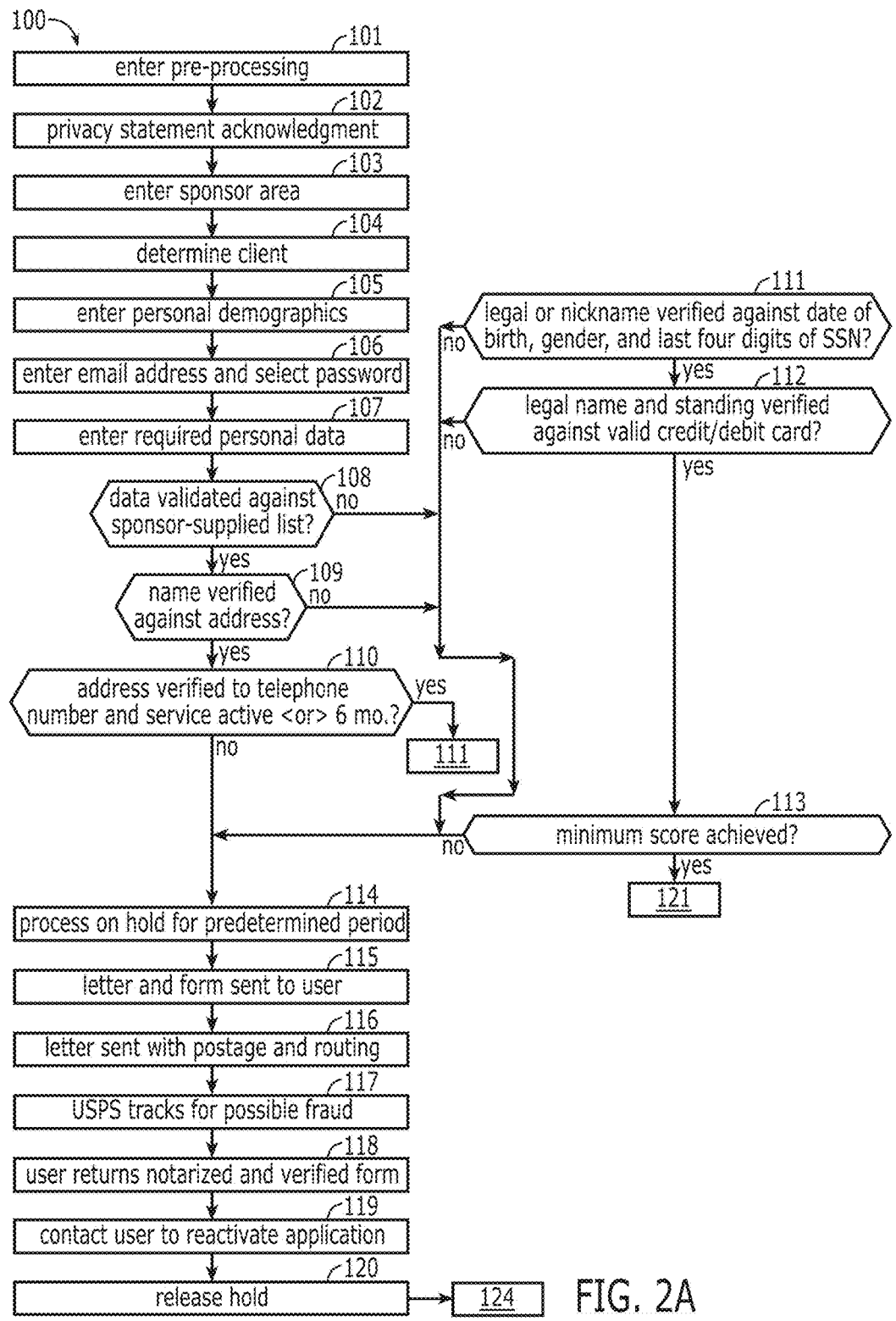
FIGS. 2A-2C are flowcharts having expanded details for the process and consent management system of FIG. 1.
Figure 2B:
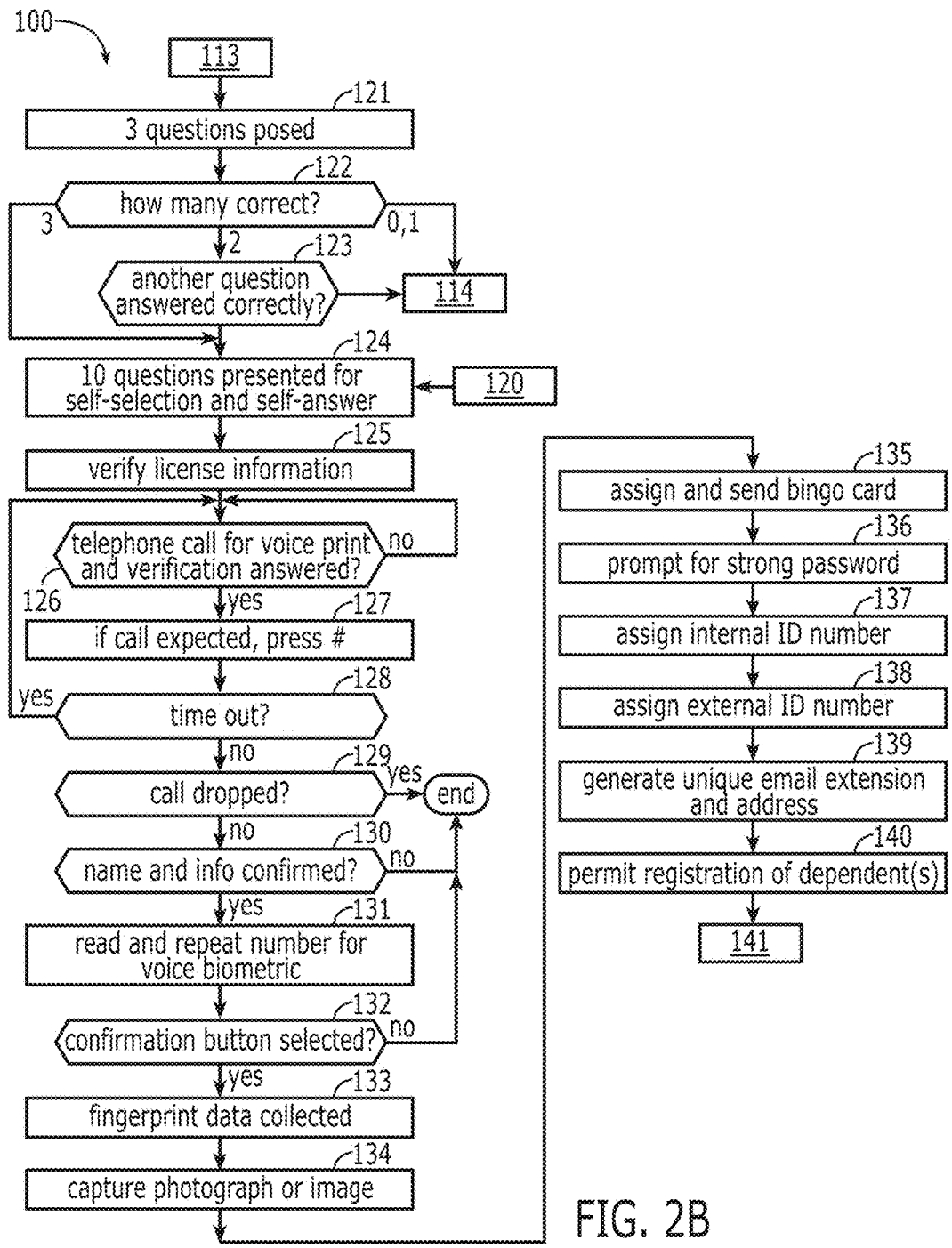
Figure 2C:
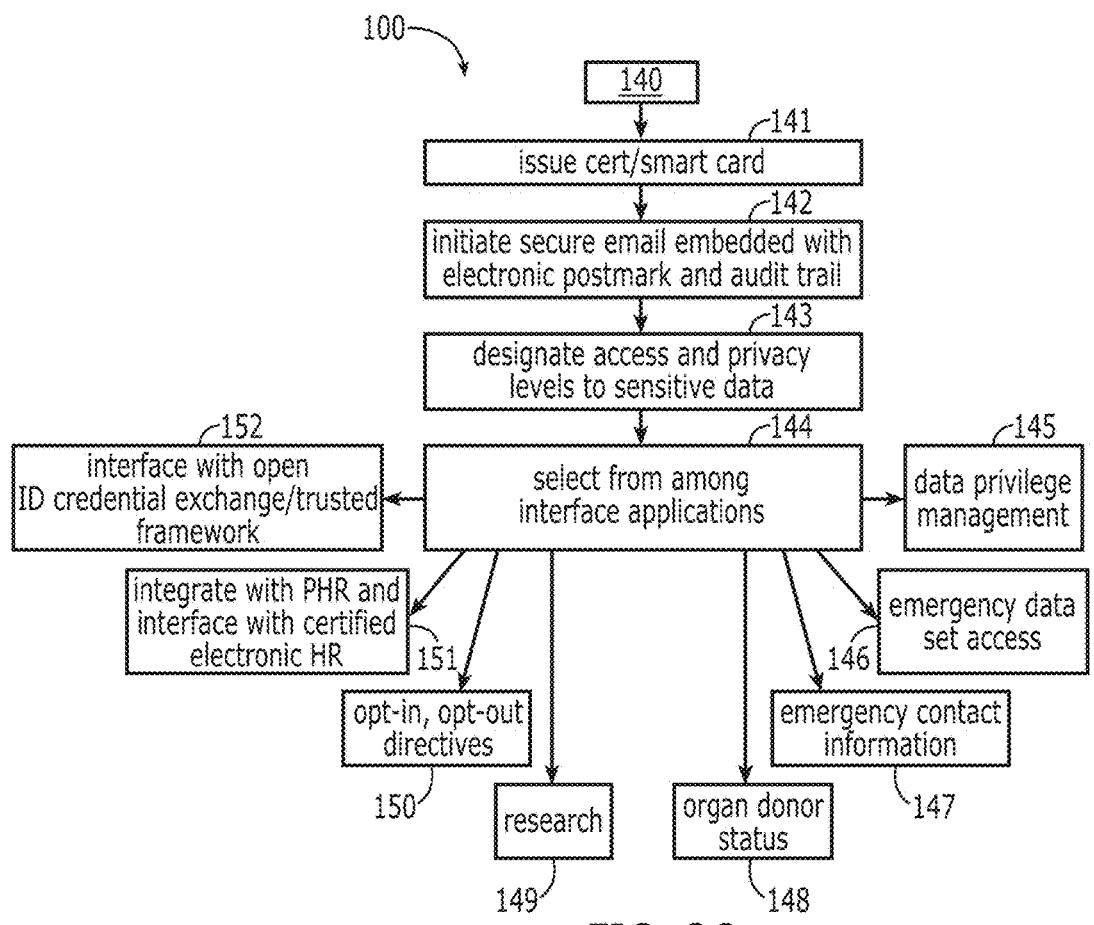

A description of embodiments will now be presented with reference to FIGS. 1-11. An initial part of a process 100 for providing access to emergency healthcare data is directed to an enrollment or registration process for the participant. The steps in this process 100 are outlined in the flowcharts of FIGS. 1-2C, with FIG. 1 comprising a high-level view and FIGS. 2A-2C, a more detailed view. Identity proofing is an important feature of the invention, which can have a plurality of levels depending upon the degree of assurance level desired. All levels preferably include validation of address, zip code (USPS) and e-mail address, by way of non-limiting example.

A Level 1 assurance can comprise validation of a user name, with a possibly weak password being used. Level 2 can be attained with the use of a strong password and possibly a question or image with predefinition. Level 2 is most common with social media user accounts, i.e. Facebook, and as such a user can use that level 2 social credential (current LOA system) as a base line to initiate an identity proofing process. The credential in its current configuration does not qualify as an authenticated attribute without additional third party verified and validated support documents. Assurance Level 3 requires a majority of the steps to be discussed in the following. The highest assurance level, LoA 4, would require all steps noted plus an FBI background check. There is escalating time and expense to advance through each level of assurance so in order to provide flexibility and adaptability the "Plus 1" function can be added (at any level of assurance) in order to reach a preselected level of assurance that needs to be achieved. By specifying the feature and then adding one additional (Plus 1) verifying requirement there can be an increased degree of assurance so different situations can be provided by an entity's being able to select a subset of the steps of the process 100 to achieve a desired level of assurance or to achieve a desired grade level for a given class of employee, customer or executive, for example. Therefore, the invention is not intended to be limited to the totality of the steps presented herein.

An exemplary multi-step identity verification and enrollment process 100 can include a preprocessing sector (block 101), which includes a user acknowledging receipt of a privacy statement acknowledgement (block 102). As noted above, the technical volatilely generated by the Internet of Things has ushered in an era of things being connected and thus the need to place quantitative values on integrity of identity proofing process that supports the verification, validation, the authentication of attributes and the variety of multifactor biometric devices and applications that impact the user authentication process. The frontier of the digitally connected society and their computer systems that run the world are underscoring the importance of why an individual will need to protect their identity and data by first claiming who they say you are digitally so the integrity of their identity is protected as they engage social, educations and business activities, on-line commerce, the health and financial sectors along with family and friends. Nationally, users will be introduced to Identity Providers (IdPs) this year whose job it is to protect a user's core identity characteristics by verifying and validating the core attributes of a user in order to authenticate core attributes as well as to validate supporting attributes.

Authenticated Attributes may include:

Legal Name: First, Last, Middle and sir names

Address: (Home #, Street Name, City, County, State, Country, Postal Code)

Date of Birth: (Month, Day, Year) and Place of Birth if Available

SSN4 (last 4 numbers) or SSN9 (all 9 numbers)

Eye color, gender

Strong validating attributes that collaborate and directly link to the Authenticated Attributes may include:

Primary user's Smartphone or cell # (Country Code, Area Code, Prefix and line #)

Line Telephone Number (Country Code, Area Code, Prefix and the line #) and or the same for Email Address linked to user's smartphone; importance in social media on-ramp registration By way of further example, and with regard to historic user's naming configuration of a user's legal identity, in the healthcare sector, more than any other sector, a patient may have used multiple configurations of their name over the years and multiple locations in registering at a medical offices, clinics or hospitals and with each entity possibly having a different naming configuration and their own medical record patient matching of medical records number is a challenge. For example, Johnathan Jefferson Jones (legal name) may also be represented as Johnathan J. Jones, John J. Jones, John Jones, J J Jones, uses an alias as J J and has a son that is a junior, Jr. Matching medical records from different medical facilities is further compounded by name changes, i.e. marriages and devoices, date-of-births captured in different formats or numbers converted, a Jr, Sr status or a middle initial is omitted from a medical record coupled with other clerical errors and Federal Law prohibits social security numbers to be used.

As documented in the above cross-referenced patent publications, each user receiving an authenticated identity also received an external enterprise patient/consumer Voluntary Health ID controlled index number (VHID) is generated (block 138) and paragraphs 57 and 59. Recognizing users do not recall how they might have registered in at a health facility five years or five months ago or registered their children years past, it becomes an important function for a user, during the initial registration process when they are making claims as to their legal name, the candidate should be given an explanation and opportunity provide possible naming configurations to their legal name, name changes-marriage/divorce, with dates and third party legal documentation and or a nick-name associated with the legal name that can be addressed during verification process. It is recognized that claimed naming configurations may not be verifiable or able to be validated but can be recognized with in that user's Identity Registry as a related legal name attributes but only after the user has been fully vetted and authenticated. Such unique user name attributes may be of beneficial use, along with their authenticated identity and data of birth, if the user elects to aggregate their health records, now permitted by HIPAA, from different health facilities they may have visited in past years.

By way of a name change example, one may have an authenticated digital identity but its initial use may be limited to the regulated industries of Healthcare and Financial Services and to a greater extent to digital commerce. A user may receive a request from a loyal vendor where they invite them to upgrade their trade username-password and possible a biometric print (multifactor authentication) to their platform. The customer/user can now respond that they have a Digital Identity (metadata) and can ask the vendor to contact the user/customer's IdP to establish their user's trust profile using their metadata attributes associated with their multifactor authentication and also provide direction on how their privacy and data will be managed. The user's new attribute profile will be logged into the user's Relying Party Registry; P282, column 14/lines 50-51 and Attribute Registry.

By way of further example, consider Identity Providers (IdPs) and Relying Parties (RPs) interface on the Nations Trusted Infrastructure To provide a work-flow snap shot of a data exchange over the nations Trusted Infrastructure starting with an authenticated user emailing their minimal core dataset of attributes (verified and validated) to a designated site requesting access, consider the following:

A user sends their digital identity (same as authenticated identity) to a favorite site where their gate keeper, a Relying Party (RP)—0023 and Claim P232, line 50-51, performs a trust function of logging in users to a secure Health-Fitness site. The RP reviews the user's minimum identity dataset of attributes that is represented—JK, FL 32794, 1963—(metadata set 1) translated as user's initials, State/zip, year of birth. Considering the RP's first task is to authenticate the user and in doing so notes, as an example, Gender classification and Consent status are missing and sends an e-message to the user's IdP requesting additional information; in response the IdP sends metadata set 2—(G.2, C.1) translated: Gender. Male, Consent. General (executed); see FIG. 7C. By design, when two or more attribute types are in a packet they are referred to as a 'metadata set'. Having this information the RP can perform their second task, authorizing access based on the Health-Fitness entities business policies and rules. Since this process is dynamic by markets and sectors, the IdP may elect to keep metadata set 1 and metadata set 2 separate and create an Attribute Bundle that contains metadata 1 and 2 which are stored in the users secure Attribute Registry; P282, Claim column 14, Claim 1 line 41-42.

Further consider Creating Value for Authenticated Attributes and Biometric Attributes for a RP trusted data exchange.

Figure 7:
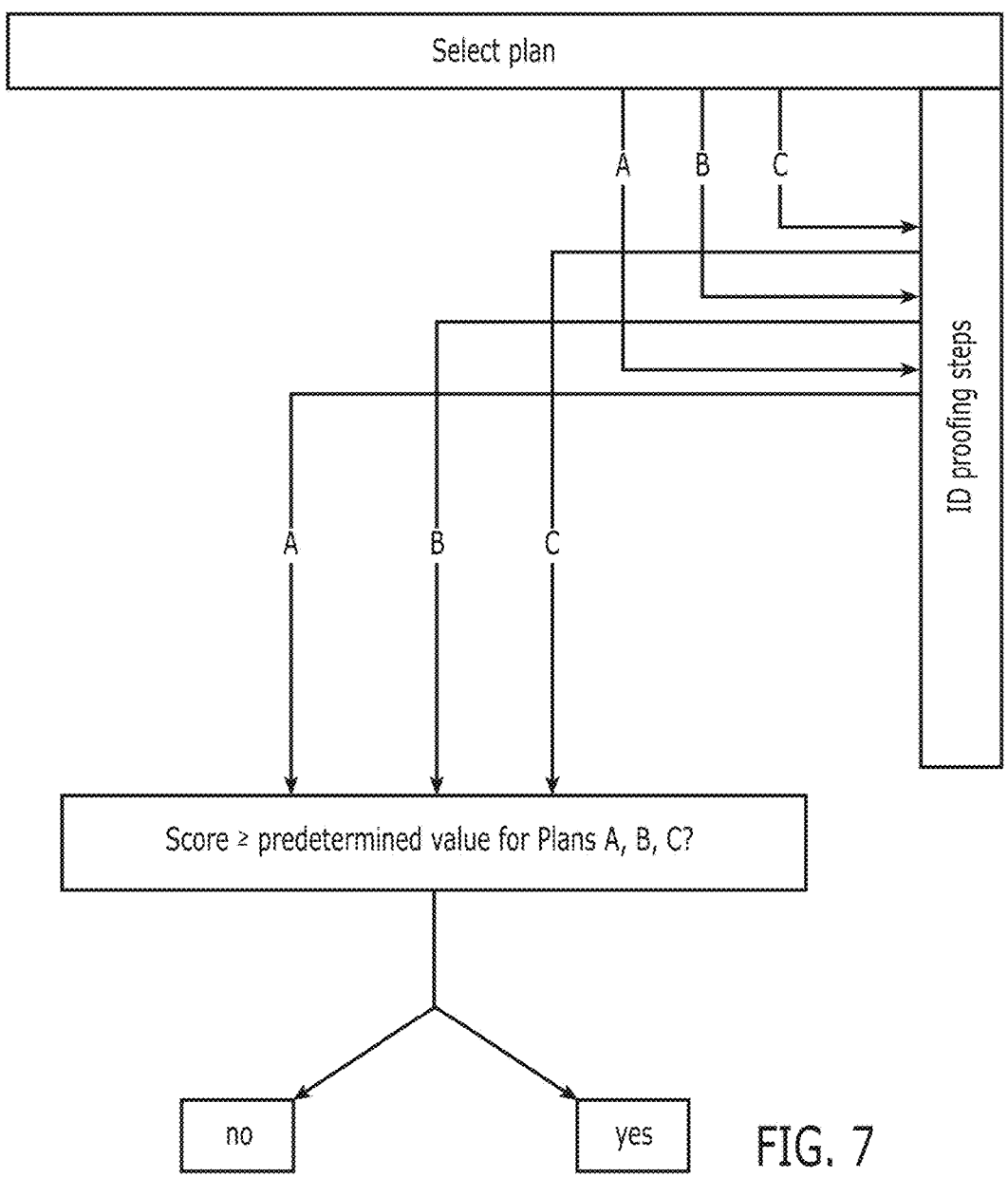
FIG. 7 includes a block diagram illustrating for a plan selection based upon a level of authentication desired, and reflects flexibility in adopting authentication levels of assurance.

To enhance the attribute value process, which was minimal in FIG. 7 (P242) Levels of Assurance 1, 2, 3 and 4, FIG. 7 needed to be reconfigured (FIGS. 7A, 7B and 7C) while keeping in place the measurement values of the X and Y axis: ID Proofing Steps and Predetermined Value scores. The revised scoring is presented as 4 Trust Levels that are segmented into 8 secondary Levels of Confidence (LOC) that are established during the identity proofing process for Authenticated Attributes that is represented by FIG. 7A. FIG. 7B also has 8 levels with a focus on Biometric-Credential Strength (BCS) Attributes as part of the identity proofing process but with a focus on biometric authentication. FIG. 7C Provides a unique Coded Value of several key authenticated personal user's attributes, that upon a Relying Parties (RP) inquiry can or will be shared without revealing addition user information. Also in FIG. 7C is the composite of 4-Trust Level rankings in a unique coded form (used in an RP exchange) based on user score values measured in the LOC-Authenticated Attribute and BCS-Attributes Biometric Authentication process and the corresponding Credential Strength for each biometric type. The Trust Value ranking is what is communicated to a Relying Party during an exchange. It is important to note that Trust Framework infrastructure RPs are the enterprise gatekeepers for access control that provides users and entities an additional layer of security assurance.

The sponsor (block 103) can have, if desired, a customized front end web application for each client (block 104). Such a personalized web ID portal directly linked to a user's personal data and identify repository, can be customized to include attributes by privacy and user class, such as emergency data/directives; financial/educational; healthcare/Rx/trials; social clubs/associations; business/professional; family-friends and e-coupons; personal/private/governmental; and mobile device registrations. One possible way of segregating the attributes is by presenting a plurality of, such as 20, pictures or graphic images, from which the user selects and names one, and provides a hint word or phrase. This selection can be tested and accepted. When the next category is selected, the plurality of pictures, minus the previously selected one, is presented from which to choose. Such a feature is classified as a 'personal factor attribute' that may be one of the attributes used in the multifactor authentication process.

A user client can comprise, for example, an agency, association, corporation, organization, club, society, company, community, group, etc. The client may or may not provide a verifiable database of qualified, IdP-vetted, persons as an initial match list used to control initial access and participant correlation.

Three general classifications of clients can comprise, but are not intended to be limited to, a consumer for family enrollment, which typically will not be vetted unless they are about to be classified as a patient; a company desiring only basic demographic-PII verification, which could use a third-party trusted site, their human resources department, a patient list, or an employee list, which may have partial vetting or not be vetted; and a company that desires a fully vetted process, requiring a personal identifiable verification (PIV) card and or a corporate ID card with smart chip, a biometric image or a bar or QR code.

The substantive part of the process 100 begins with entry of demographic data (block 105), which can include entering an email address and a selected password (for verification re-entry; block 106). All required personal data are also entered (block 107), which can include, but are not intended to be limited to, such as name, address, citizenship, social security number, etc.

A verification request screen provides the ability to perform further validation against sponsor supplied list (block 108). Acceptance may be recognized by elements such as a government-issued ID; driver's license, Medicaid, Medicare or Food Stamp card, a PIV card, a Green Card, or a passport with a magnetic stripe or bar code that can be swiped in a reader and electronically present a matching name. In addition, or in lieu of this, an employer, membership club or organization that issues magnetic stripe card can be used as a secondary validating source.

Due to digital automation and the explosive acceptance of social media with 50% of the population having social identities that requires minimum demographic data, user name, address and a password, such are being recognized as baseline qualifiers when used with a one-time-number/password (OTP) for initiating an IdP starting the authentication process with user focused knowledge based questions, a process recognized as Knowledge Based Authentication or KBA.

Consider the undocumented individual, by way of further example.

By way of example, an undocumented for the most part have no identity and therefore no Level of Confidence (FIG. 7A) in their identity to speak of but if a community support group steps forward to lend their support in helping establish some minor credibility towards the undocumented self-asserted user data that could provide a user with a minimal LOC 1 to aide in opening an account for the user for both healthcare coordination and social service benefits.

But if the undocumented user has frequented local public health clinics for their services, Community Service Centers, other community organizations like the United Way, First Harvest Food Banks or the Salvation Army for food and shelter, along with faith based service centers surely this Undocumented user is 'known in the community' by licensed community social and health workers. These organizations do receive Federal, State and Community funds and do document those they serve in order to receive future funds. They also have basic computer systems with network connectivity that is usually coordinated through county or city government centers or by designated organizations like United Way. These local social community networks protects these support entities from being hit by repeated 'frequent flyers' with sad stories hoping to receive handouts; these organizations do know many of the undocumented by appearance, first or nick names. Additionally, these types of Community Service Organizations are registered with the State and licensed by a County or City with a registration license as a community service entity meaning these creditable service organizations and most have Level of Confidence of 5 rating as does the business owner. This information and knowing professional social and health workers do work with these entities along with health clinics and emergency rooms there is a community web that do know who most of the undocumented are.

That given, if two or three cross mix of these community entities (a health clinic, a social service worker or professional and possibly a third community service organization) can say they recognized the undocumented as having been in the community and vested their facility and as such those individuals could have a derived-vetted identity, Trust Level 2, a Derived (LOC2), so a health account can be created for the Undocumented User as long as that individual is willing to have a digital facial image captured and a biometric hand or finger print taken so the user can apply a biometric image to an e-consent as to receiving health service personal account possible coupled with an incentive. The personal health account is the user's account and access has been granted to health care professional and social workers by the user within that community of care. This activity can create a personal health record account for that undocumented person within the community for the benefit of the individual, public health, the healthcare system, and for the community. The local community organizations can check a community registry and note that the undocumented is registered in the community network but they cannot access the account without qualified credentials.

The verification process begins by verifying the user's name to his/her address (block 109), which can comprise a third-party verification of the entered street, and then verification of the user's name to the street. This step 109 can be performed, for example, by the U.S. Postal Service (USPS), although this is not intended as a limitation. If the registration candidate is using a self-asserted social identity as a base level for launching an identity proofing process the KBA will generate three consumer-based questions are presented (block 121), such as, for example, third-party-providing knowledge-based questions that relate personally to the candidate's past history, for example, vehicles owned, places lived, government services used.

The user's entered address is also verified against the entered telephone number (block 110). If desired, an additional set of steps can comprise validating the user's first telephone number with their carrier, and, the telephone number has been active for less than 6 months, the number can be validated to an address, with the verification of the carrier. Considering the wide adoption of cellphones and smartphones, land-lines are declining so validating both land-lines, cell and smartphone numbers is now part of the validation process.

Next, the user's name is verified against the date of birth and gender along with the last four digits of the social security number (SSN; block 111), which will typically comprise a third-party verification.

The legal name of the user and his/her standing is also verified with a valid debit or credit card via a third party, such as a national financial institution (block 112) or a bank issue EMV smartcard that has a chip that can also accept a PIN code or an e-signature. This will typically not entail a financial transaction, but rather the return of just a yes or no response of good standing.

Depending upon the assurance level requested a positive acknowledgment from steps 108-112 must be met to a minimum value (block 113). It is recognized Trust Level (of Assurance) 2 does have a lower threshold for a minimum value for qualifying for a Trust Level; see FIG. 7C. It is recognized that many user/candidates might be challenged in obtaining an authenticated identity since they only have self-asserted social identities and limited or no identification but the majority do have a cell or smartphone. Since the national goal is to assist all candidates in having a base level of identity, candidates can qualify for a derived identity through the assistance of social workers, local community outreach programs and health centers, FIG. 7B. In these cases biometrics images (face and finger prints) play an important role in validating the user as does the use of one-time passwords/code (OTP) provides a critical function in sending a one-time query-time sensitive response to the user's smartphone which is also the user's personal hub for other social and community benefits such as food stamps, medical benefits (Medicaid) and housing assistance.

Otherwise, the process is placed on hold for a predetermined period, for example, for up to 45 days (block 114). In this case, a letter and form are electronically sent to the user (block 115), who is asked to return the letter with postage and routing data (block 116). The carrier, for example, the USPS, tracks the letter for possible fraud (block 117), thereby providing third-party notarized verification.

The returned form letter will typically be required to be notarized, the credit/debit card verified, and mailed back to a designated address (block 118). When internally received, the form is date stamped and recorded. A message, such as an email, can be sent to the user, providing a personal access code to reactivate the application (block 119). The hold is then released "manually" (block 120) and the process 100 continues from block 124, joining those who had achieved the minimum score at block 113.

Consider a Virtual IdP session with a user and a Trusted Notary, by way of further example.

Given: The distinction between in person and remote identity verification is becoming blurred with the enhancement of video-conferencing, i.e. skype and others, and smartphone based video cameras. With an array of connected technology, providing third-party notarized verification (block 117) becomes an important authenticator in the identity proofing process.

Notary law is governed by each state and the majority of states will not accept adjacent state notarization and only two states accept electronic notarizations. Because of the uniqueness of the identity proofing process a notary must be 'trusted' meaning they must have a Trust Level 4 standing to qualify for a digital notary designation and be certified by the American Society of Notaries as a notary's understanding of the Guiding Principles of the National Strategies for Trusted Identities in Cyberspace (NSTIC)—Presidential Directive and the supporting compliance guidelines for Privacy, Security and Interoperability as reflected in the National Identity Ecosystem Framework (IDEF) document. Hence the designation: Trusted Notary.

For an individual who elects to go through the IdP process using their smartphone, the individual must first initiate an on-line registration process by providing their claimed core demographic data for verification and validation. If approved at that point in the IdP process, a candidate user will be provided a consent to sign stating the make and model of their smart phone, their cell phone number and requested to send an image of their driver's license (DL) to a designated number, an email address along with close up facial image (selfie) of themselves as an attachment which a notary will print and will be compared to the actual person during the on-line session. The executed consent will also grant permission for the trusted notary to access a state's on-line DL database in order to validate a user's core identities and the expiration date of their DL. Upon receiving all information requested, the trusted notary sends a virtual on-line number for the user the call providing a 15 minutes window, by way of example, for the call, a start time, a check box agreeing to the process and confirmation the user can receive and send text messages and emails.

As the call starts, the trusted notary makes and introduction and validates the user's demographic data on the DL with core authenticated data that was done before the on-line session started. The DL itself is not validated in this session but the trusted notary does record the DL # and the expiration data for later verification as to its validity. To close out the session, the last step is to send the user a One Time Password to acknowledge that the sessions have taken place, that the users email address, cell number and the affirmative response received is time-date stamped as a confirmation, and verifying that the session took place under the direction of a trusted notary. Such will be bound to the user's Identity file and logged into the users Identity Registry.

In a similar fashion, but only after the initial authenticated user Identity has been established, an authenticated user acknowledges having several aliases, one that is frequently used in their professional, political or sporting environment where trust, integrity and image are meaningful and thus would like to have that alias name authenticated as an authenticated attribute. To achieve that goal requires an in-depth review and a certified audit trail by an independent third party that will sign and have notarized by a Trusted Notary that reflects the use of the alias name in different settings. Once the vetting process is complete, it will be further documented by a sworn authenticated user's consent statement before the authenticated alias name is bound to the authenticated user's identity and their primary user device before being logged into the Identity Registry.

The involvement of a trusted notary during an identity proofing process can enhance a candidate user's Credential Strength Value; P282, Notarization 0045-0046, FIG. 2A, block 117-118.

By way of example, if the minimum score was achieved at block 113, three consumer-based questions are presented (block 121), such as, for example, third-party-providing knowledge-based questions. Depending upon the number of correct answers (block 122), the process 100 proceeds as follows.

If all three questions are answered correctly, the process continues at block 124. If only two questions are answered correctly, a fourth consumer-based question is posed (block 123), and, if this is answered correctly, the process proceeds to block 124. If either the fourth question is answered incorrectly, or only one of the three initial questions is answered correctly, the process 100 returns to block 114, wherein the process 100 is put on hold.

The process 100 for those who have satisfied the above conditions by presenting a plurality, for example, seven question options for self-selection and self-answer (block 124). The user's choices are captured and maintained for future use as a means of validating a user who might call a health coordinator or a support desk.

Another aspect of the process 100 can include the verification of professional licensing, designation or credential information (block 125), such as those that the user may have acquired through training, schooling, and/or certification credits that can be issued nationally or in some other verifiable manner. Such licenses can include, but are not intended to be limited to, licenses to practice medicine, carry a fire arm, perform law enforcement duties, perform financial auditing services, carry out a professional trade, etc. These credentials can be validated, for example, via a recognized third-party credentialing service, and preferably will include an expiration date and certificate number.

A further aspect of the process 100 includes the placement of a telephone call for voice print and verification, which can comprise an out-of-bound third-party process (block 126). If there is no answer, the call can be repeated a predetermined number of times, for example, once. Preferably the user will have provided the telephone number to be used while the user is at a computer screen.

If the call is answered, the user is asked if the call was expected (block 127), in which case the user is asked to depress a telephone key, for example, the "#" symbol or provide a one word response—Yes or No to activate the telephone call part of the process. If a voice command or the symbol is not pressed in a predetermined amount of time (block 128), the process ends, with a predetermined number, for example, one, repeat call, to be verified, allowable to the same telephone number. If the call is dropped (block 129), the process ends, and the user is requested to call the host, via, for example, a help desk.

If the call proceeds properly, the system repeats the user's name and confirms the entered data, and records the user's acknowledgement (block 130). Again, if there is no response, the process 100 ends. The user is asked to read and repeat the telephone number, in order to record a voice bio-metric (block 131). Then the user is asked to confirm that they provided the requested data by selecting a button (block 132). Again, if there is no response, the process 100 ends.

The process 100 continues by collecting a biometric of a user's fingerprint or a facial, iris or another type of biometric print/image type of information with the use of a validated and approved third-party vendor, for example (block 133). The process 100 also includes the capture of the user's photograph and/or other type of image/graphic that has a named definition (block 134). Pictures or graphics could be provided, for example, by a qualified third-party vendor but the user must brand such with a defined term, event or phrase.

The process 100 then proceeds by assigning a random "bingo card" to the user. The bingo card can be printed and transmitted to the user, for example, by a third-party vendor (block 135). As an example, a card having a mag-stripe, bar code, OR code or RFID functionality could be employed that interfaces with preapproved authorized forms for consent management and privilege granting. It also can be used as a medium for a one-time password or code (OTP).

The user is then prompted to devise a strong password for user authentication (block 136).

Next, an internal unique identity number is generated and assigned (block 137) in concert with defined authenticated attributes. Also, a separate and distinctly unique, external enterprise patient/consumer Voluntary Health ID controlled index number (VHID) is generated (block 138) and used as an external user identifier that can be placed on a user's primary smartphone or on different types of token devices. The external identifier must be electronically protected so it is only applied through a two or multifactor authentication process. The external identifier incorporates privacy and consent restrictions that originate with and correspond to a user's internal requirements that are the primary triggers set by the user. The Internal identifier empowers the user navigated their personal health data and supporting applications using their digital identity in addition to managing privacy preferences and the sharing of restricted content such as protected health information, such as directives and emergency contact data. The external ID is an electronic pointer to a user's account, it does not grant access, and it only reflects the user's privacy security preferences to the one requesting access and is known to the user having an established digital identity and a validated primary smart device such as a smartphone or laptop. The latter is critical point in the patent process as reflected in FIG. 11 that tags every device with an IP address (IP Class with mask, Full IP, Sub IP, partial IP.,) and each IP address is preregistered in a Device Registry and linked to the user/owner or other individuals who are prequalified for access to a user's account and those requesting access. Each device also is tagged with a Privacy Classification. If a user elects to share a segment of their clinical health data for research or for the benefit of community health, they, through the anonymization function, de-identify their protected health information can do so using their smart device with multifactor authentication and the OTP function.

A unique secure email extension and address are generated (block 139) that function separately, for identity protection, and are separate and distinct from the current "user name," which is the email address used in the identity proofing process. This process can use an electronic post mark for emergency care patient tracking, incorporating the HITSP standard and using CCR and/or CCD record-tracking functions.

If desired, the user can identify and register dependents (block 140), such as minors, dependent seniors, or disabled persons under his/her full-time responsibility and direct care and who might, in an untimely accident, need to be identified and the care of whom would require access to their emergency data.

Once the user's identity has been validated via the foregoing steps, a digital certificate can be issued, for example, by a Certification or Attribute Authentication Authority (block 141). Roaming certificates or Authenticated Attributes bound to pre-approved PCs, lap-top or a smart digital device such as cell or smartphone can be server-side based, and digital certificates, personal privacy and security attributes, can be integrated into smart ID cards and vetted digital devices in compliance with national NIST guidelines and FDA proposed regulations and HHS enterprise security and infrastructure exchange regulations and guidelines.

To complete the substantive validation and registration process, a secure email function is initiated that is embedded with an electronic time-date postmark and audit trail for secure data exchange (block 142). The trusted process validates the user's ID and provides an authentication process with electronic and digital signature functions (when using higher LoA's or the new Trust Levels FIG. 7C) and an e-audit function for non-repudiation. The process, which is preferably encrypted, focuses on access controls and privilege management using electronic marks integrated into each secure communication. This can apply, for example, to emergency data, a clinical trial, a financial transaction, secure document sharing, a "do not resuscitate" order (DNR), or a legal document exchange that utilizes multifactor authentication coupled with user executed consents.

The user is permitted to designate levels of access to sensitive data, preferably in customized fashion (block 143). The user is asked to select a combination from among elements such as username and strong password plus one or more of the bingo card, a biometric ID, knowledge-based questions, the user's image, and digital signature, although these are not intended as limitations.

The user can also select from among at least the following interface applications (block 144) including: user preference relating to data privilege management (block 145), emergency data set access (block 146), emergency contact information (block 147), organ donor status (block 148), research (block 149), and opt-in and opt-out directives (block 150). The data can be integrated and stored in their certified personal health record (PHR) and interface with a certified electronic health record and hospital-medical office patient portals (block 151), if desired and available. The data can also interface with an open ID credential exchange and the national trusted framework (block 152).

Figure 3A:
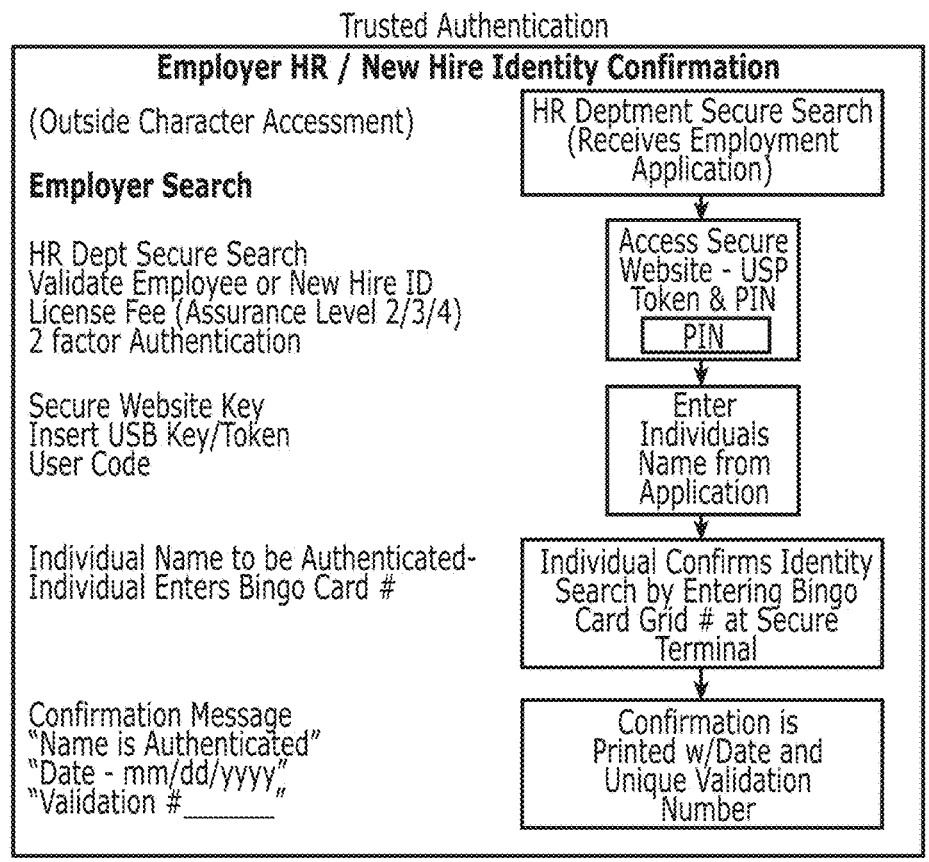
FIGS. 3A-3C are block diagrams illustrating trusted authentication, including employer/new hire identity confirmation (FIG. 3A), hospital search/emergency department (FIG. 3B), and registered first/volunteer responders (FIG. 3C)
Figure 3B:
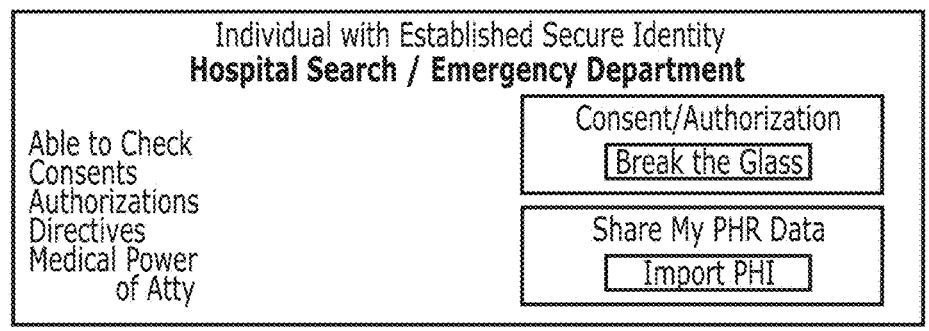
Figure 3C:
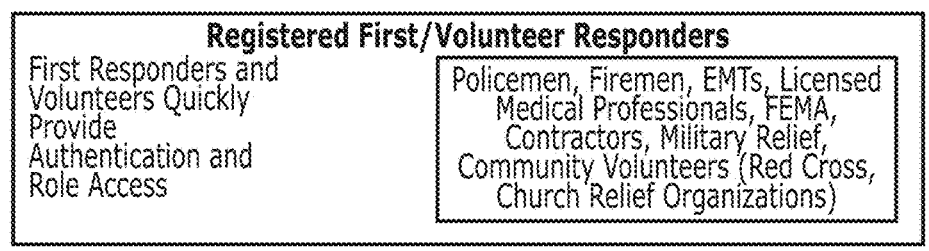

FIGS. 3A-3C illustrates the three types of trusted authentication: employer/new hire identity confirmation (FIG. 3A); hospital search/emergency department (FIG. 3B); and registered first/volunteer responders (FIG. 3C).

Figure 4:
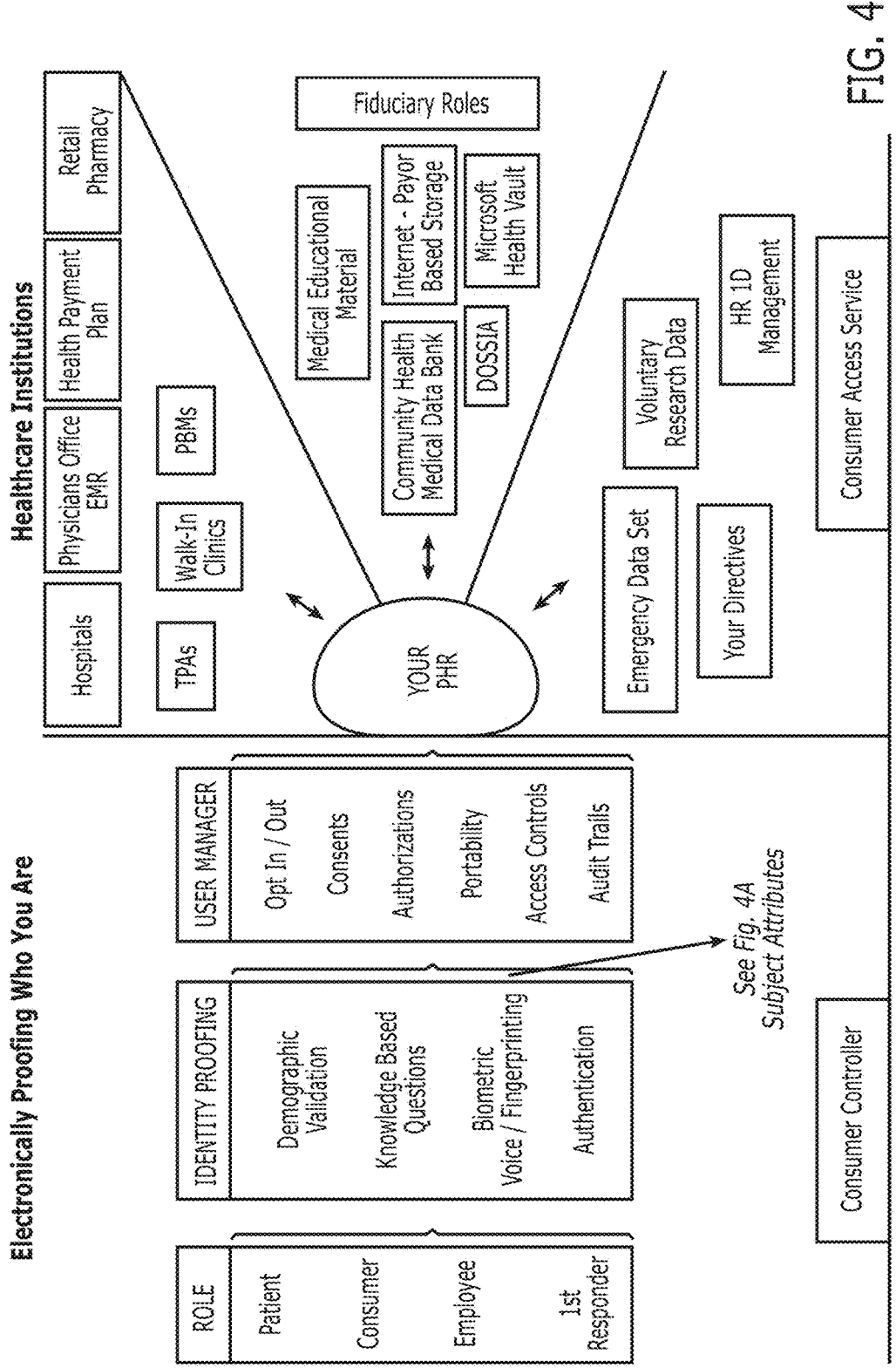
FIG. 4 is an authentication flowchart of one role-based identity proofing system illustrating an interaction of a personal health record with a healthcare institution.
Figure 4A:
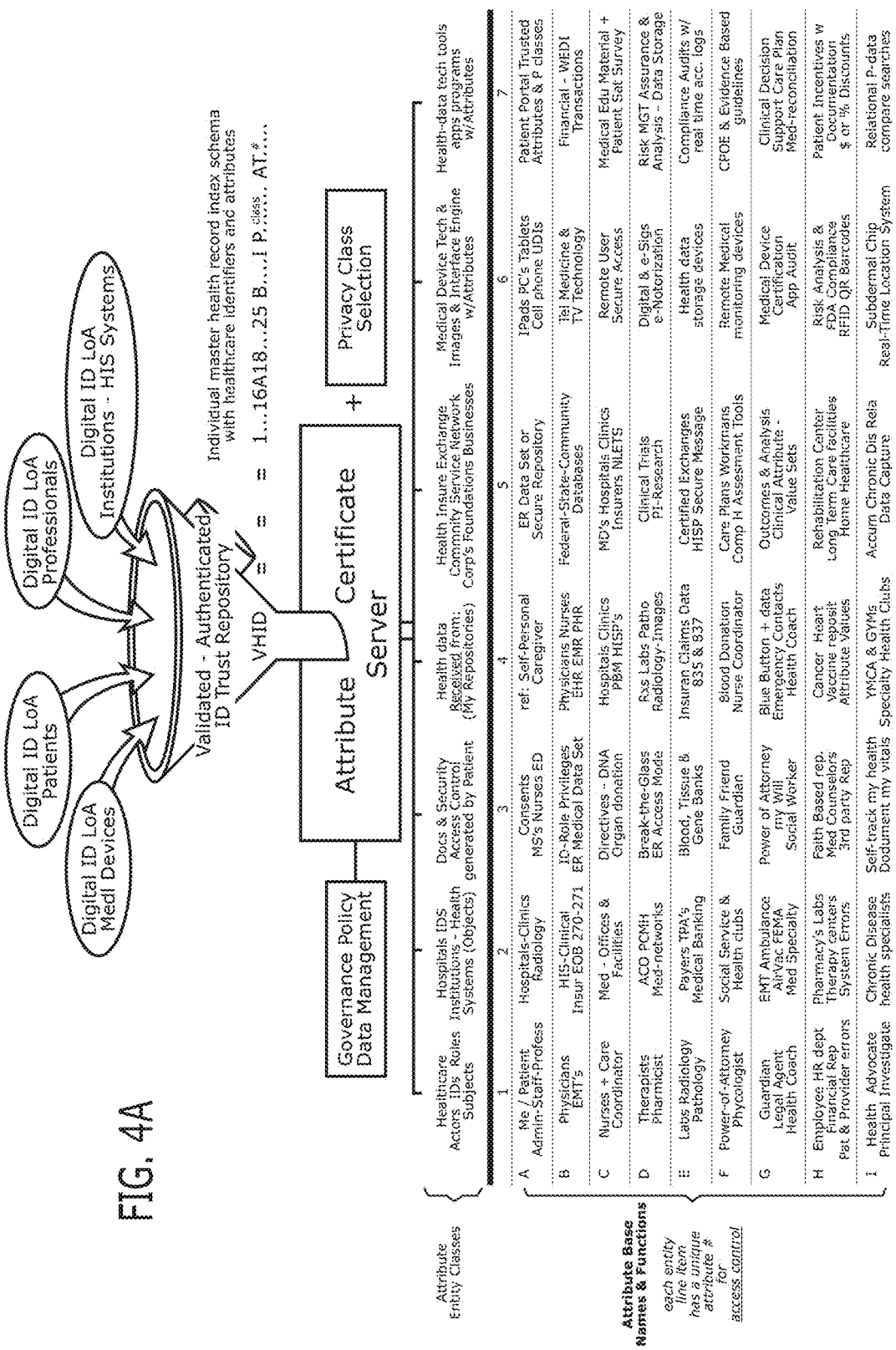
FIG. 4A is an Attribute functional matrix for one line item Role Based Access Control and Privacy Class data management illustrating a patient ID and relational entity attribute structure with designated functions for access control, by way of example.

FIG. 4 is a flowchart of role-based identity proofing and the interaction of a personal health record (PHR) in order to populate the Emergency Data Set (FIG. 8), a subset to the PHR, to make available to emergency responders and hospital emergency departments. It also provides a platform to send and receive health information for doctors and healthcare institutions. Data flow that is controlled by the consumer (left-hand side) is shown as contributing to the participant's PHR health data repository, which informs and tracks the consumer access service to the network, has the ability to receive alerts, notices or copies of medical records or emergency reports from providers, a hospital or a clinic and story the PHI in their health data repository account FIG. 4A provides the participant with user roles, functions and attribute entity classes linked to privacy class attributes so a user can control, share and manage their health information.

Figure 5:
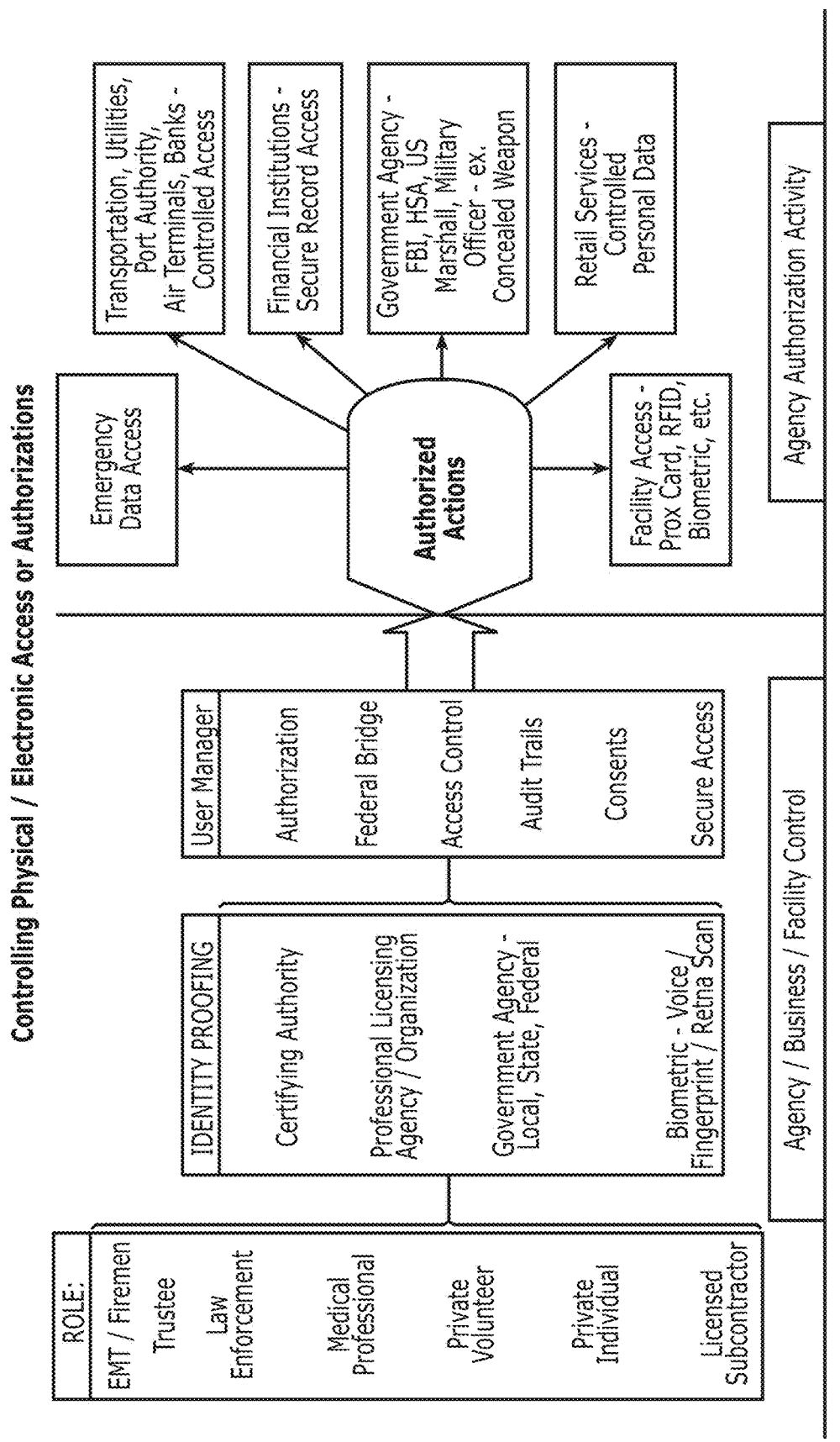
FIG. 5 is a flowchart illustrating a controlling physical/electronic access or authorizations.
Figure 5A:
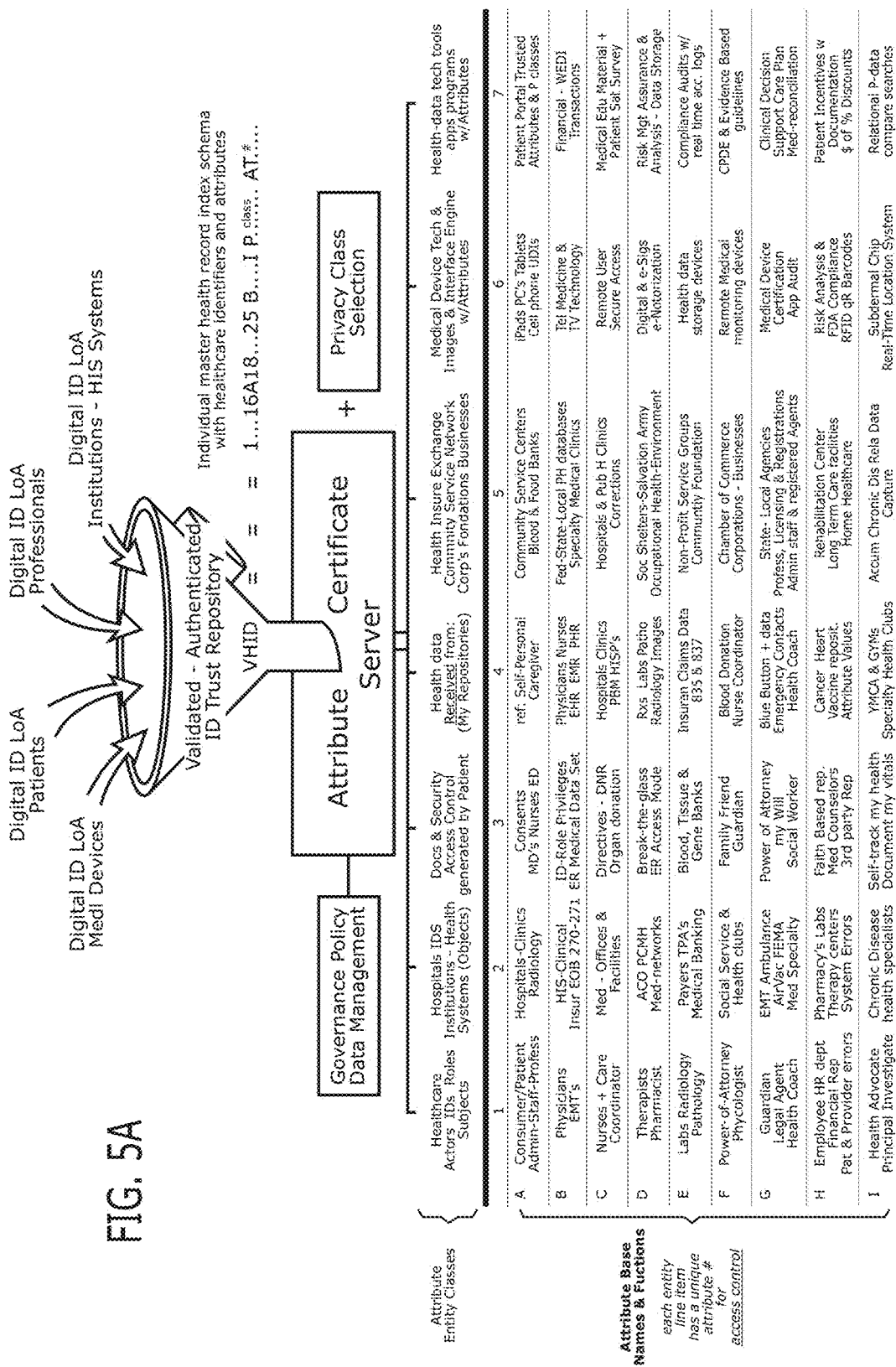
FIG. 5A illustrates one digital object ID with relational attribute structure and designated privacy and access control functions for a "health-e-community," by way of example, with a focus on registered third party entities, enterprise, organizations, human resource departments, health information service provider (HISP), identity providers, relying parties, defined repositories, associations, clubs to include government agencies, insurers, institutions and trusted authorities.

FIG. 5 is a flowchart for controlling physical/electronic access or authorizations. Here are shown the different roles of the participants, leading to their respective authorized actions and access that interface with the participant.

In use, upon the occurrence of an accident, for example, typically the police are the first to arrive and notify emergency medical services. An ambulance can be dispatched, and the police attempt to identify an unconscious/unresponsive victim. This can be attempted using the motor vehicle registration records, such as VIN#, Tag#, or DL #. The vehicle identification number is used to query a federated emergency contact registry (for example, NLETS), to obtain the vehicle owner emergency contact name(s) and telephone number(s). These data are passed to the emergency responders, who can search systems for possible historic patient data.

In a particular embodiment, the VIN# registry can comprise a stand-alone system that interfaces with a state's driver's registry and interface with NLETS. An individual who registers his/her VIN# can voluntarily elect an "alert function," enabling a law enforcement office to be alerted via, for example, a red flag, that emergency medical data are available and can alert an EMT. The user can also create an emergency medical data set, using their PHR, provided when user enrolled, and can elect not to have a flag posted.

The emergency medical data set is formed as a subset of a personal health record (PHR). These data should preferably be stored on a separate secure registry, which can only be accessed by a licensed emergency professional (e.g., EMT, nurse, fire EMT, physician, ER staff, and trauma center personnel). An identifying and permission-granting technology such as a voluntary health ID (VHID) is incorporated into the process and grants access via multifactor authentication when a request is validated and approved which is a prequalification for licensed EMT's and first responders. As illustrated in FIG. 3C, a separate registry can be provided for licensed emergency medical professionals.

If the victim's identity is established and has consented, in advance, to use their functional and privacy attributes to make Emergency Medical Data available in case of an emergency, a membership in the network is ascertained, in which case an emergency dataset is provided to the healthcare worker. The patient can then be treated at the scene and in the hospital in a more informed manner. The NLETS data are also used to make contact with those listed in the emergency contact registry.

Consent documents can also be included in the system, such as, but not intended to be limited to, VIN#, medical ER Content-driver's license Content, emergency medical dataset, "break the glass" consent/authorization, organ donation data, and DNR data.

To validate the user's demographic information at a future date, once a user is fully vetted and authenticated, a unique email address is generated that will incorporate the alpha text of their email address to the left of "@" followed by a forward slash (/) mark, at which time their validated address will be inserted excluding state and including zip code immediately followed by @. After the "@" mark will be "USPS.GOV>" (sample: jkragh/1024orangeaveorlando32802@usps.gov) encrypted. At a future date both this email (address inserted) can be sent to the USPS to validate its authenticity accompanied with an attachment of a new address of the user if such applies. This process is for authenticating and revalidating an authenticated ID or "elink authentication." If USPS discontinues this service, a private, secure and un-published national e-mail service provider will be utilized.

In summary, the system and methods of the present invention permit the establishment of a trusted process for interoperable identity and access management in a distributed healthcare enterprise. The system and methods provide ID proofing, vetting, validating and authenticating attributes and leveraging vetted authenticated devices, cards and tokens linked to a user to be usable in a distributed interoperable knowledge healthcare environment. The invention uses one-time passwords and codes (OTPs) and multifactor authentication (MFA) features to help a user in managing their identity and sensitive information.

The key principles include ID proofing, generating new identity reference/tokens, or recognizing and accepting existing ones to provide contacts and directives. A trusted process incorporates functional, institutional and privacy attributes, and authenticated attributes, linked to participants digital ID is included for generating an enhanced token in compliance with Federal Guidelines and Regulations and established policies. Real-time authentication or verification of identity are coupled with privileges and attribute based access control with authenticated attributes and supporting attributes for devices, things, applications, objects, subjects and events, as well as supporting policies governing "rules-of-the-road" coupled with "best practices" as applicable across multiple trusted domains, medical professional, and healthcare user communities to address medical emergencies and disasters. Communities and organizations define their own policies, rules, privileges, and criteria, which can be distributed. HIPAA, state, and stimulus guidelines are followed, offering a common foundation for recognizing authenticated identities in a variety of public and private healthcare settings across the national landscape, and even internationally. Trusted Notaries will have a pivotal role to play in local communities to assure compliance to Trust Framework governing guidelines of the Identity Ecosystems Frameworks Interoperability, Privacy and Security rules.

Clear definitions of trusted "rules of the road" and recommended policies are provided for adoption in healthcare, and the ability to apply the rules consistently within local, enterprise, and federated architectures. This provides a cross-cutting functionality, which addresses the typically inconsistent methodologies inherent in current healthcare facilities. A foundation for privilege and attribute management is provided, which can include an expanded reach with business associate agreements, certified personal health records, and certified electronic medical records.

Further, consistent implementation is balanced with potential cost/risks. The system and methods have appropriate levels of trust/assurance, with both identity and assigned attributes. A common foundation is also provided for education and promotion, and a cost-effective process for a more common risk-management framework.

An exemplary privacy class matrix is depicted in FIGS. 6, 6A, 6B and 6C illustrating elections that can be made by the user regarding privacy levels (to share all data, restrict data sharing, share with restricted access, no sharing of data, and emergency-only sharing of data). Any number of classes can be devised for each of these privacy levels, so that a user can select a privacy level over a multitude of domains, such as a disease state.

Recognizing that not one size fits all in proving one's identity, an organization or individual will have a choice in selecting the strength and integrity of the ID proofing plan they will go through, as discussed above. Following the NIST guidelines, one can select a strong authenticated ID (FIG. 7) Plan A that requires more steps in the ID proofing process and represents a higher level of "trust" than if one elects Plan B, which represents a less rigorous level of identity proofing, resulting in a moderate level of authenticated trust and therefore requiring a fewer number of steps as in Plan A. If a lower level of a trusted ID is desired (below Plan B) and only a few steps in the identity proofing process are needed, then Plan C would be utilized. A group or an organization may also elect to have a customized program of steps (FIG. 7) that must be used to achieve a passing score to achieve a desired authentication level, by way of example.

The focus of this activity is to place users in control of managing their identity, controlling access to their information as they engage the digital community while also recognizing how a RP will utilize authenticated and non-authenticates in a connected market to grant access. But there is a challenge, not all authenticated attributes, attributes and biometrics are equal hence they should not be grouped or bundled as equal values and under one LOA grouping (FIG. 7) process as they are. For a user's digital identity to be trustworthy it must be authenticated and be accepted in environments, cultures and communities of interest where the user is located based on a measured value associated with each authenticated attribute, device along with other attributes including biometric, which are common place in a digital market today.

It is recognized that attributes having been verified and validated, and some authenticated, a user can navigate different settings by customizing their digital identity attribute profile by selecting attributes from their Attribute Registry (P282) to create a unique Meta-data profile for a health insurer, hospital, employer or a social research site. What provides meaningful value to RPs is the Level of Confidence associated with each authenticated attribute and the Credential Strength Value for each of the Biometric attributes that determines the Level of Trust ranking.

Many classes and types of Biometrics have been adopted by the digital community but all are not equal though they do have one thing in common, they are recognized as a user's 'authenticator' in a two-factor authentication process replacing the outdated user-name and password. The combination of a shared secret and a biometric is recognized as 'multifactor authentication' process which is in vogue and trusted in the digital market. Hence, knowing a user's individual's identity should never be shared during a digital transaction, the need to transform from Levels of Assurance to Levels of Trust values that are supported by aggregated attribute values creating a trustworthy factor that RP's can quickly assess and trust.

Consider FIGS. 7A, 7 B and 7C interrelationships: FIG. 7A, Verifying and Validating the Authenticity of Identity Attributes; FIG. 7B, generating a value as a result of verifying the Authenticity of Attributes related to Biometrics, Devices, Tokes, Sensors, Applications, Bar—QR Codes and others so a user can designated which element they will use as Authenticators for gaining access based on a Trust Level Vale and FIG. 7C, the algorithm that configures the Trust Level of one's Personal Dataset, their primary authenticated device (smartphone) that is bound to the user's Digital Identity and linked to verified and validated sensors, applications and other object features preapproved for use.

By way of example, consider following the Enrollment process where piece code (digital security elements) is transmitted to the user's pre-approved smartphone or other user hub device along with their personal Voluntary Healthcare Digital ID that enables electronic access to their Personal Emergency Medical and Contact dataset along with their own Personal Health Record (PHR) application, the content which they will own, control and grant access to.

After a user has populated and digitally signed one or both of the Personal Emergency Medical and Contact datasets, both a digital security element and a piece of micro-code will embodied with in the user's smartphone device in the emergency contact section and or on a PC in addition to the respective piece of Emergency Dataset being sent to NLETS and Dept. of Homeland Security, FEMA. In working with the Telco's, a piece of code will also be sent to them for incorporation into their ICE application on the smartphone for access by EMT's, Police and ER professionals. Smartphones, regulated by the FCC, are the only mobile device recognized that can provide a strong level of internal biometric security across networks for the ICE (in case of emergency) function to other government agencies. Secure sites and licensed professionals like FEMA/DHS, NLETS, local EMT's, law enforcement and medical professionals during untimely events can use their credentials to access the ICE user data on a user's smartphone at any geographical location nationally. ICE data must be consented to, time-date stamped and digitally signed.

Regarding FIG. 7B, a number of Biometric technologies are noted and a user may elect to use any combination of biometric devices unique to a designated setting or environment that would be so designated in the users Biometric Registry. To be logged in the Registry the biometric device must be classified, verified, validated and possibly authenticated to a base Standard, NIST Guideline, FDA, SANS or IEEE engineering guideline, depending on its purpose. Once the process is successfully completed the attributes, which may be authenticated, will be bound to the user's authenticated identity and logged into both the users Identity Registry and their Biometric Registry along with the Value ranking achieved as reflected on the FIG. 7B matrix.

Typically, each plan will have a scoring process associated with it in order to achieve a plan-designated authentication scoring level. An individual will know steps in advance that will assist in helping one achieve a designated score that can be independently validated and audited. The resulting score of an identity-proofing process then results in a pass or no-pass score.

FIG. 8 is an exemplary emergency medical data set layout of the present invention digitally or electronically signed by someone with access to the entire record.

Figure 9:
FIG. 9 is a portion of the data set (contact information) of FIG. 8, with the emergency medical data set hidden from view.

FIG. 9 is a portion of the data set of FIG. 8, with the emergency medical data set hidden from view.

Figure 10:
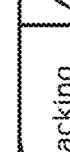
FIG. 10 is an exemplary screen shot of an exemplary portal for generating data in a user's personal health record.

FIG. 10 is an exemplary screen shot of an exemplary patient portal for generating an Emergency dataset which is a subset application that is part of user's personal health record.

By way of further example, the forgoing matrix graphics of FIGS. 4A, 5A, 6A, 6B and 6C as representing relational steps associated with a patient/actor using their Digital ID in granting access and viewing privileges to their PHI. When a cell in one of the matrixes is selected (a Column-Row alpha-numeric construct) by a patient, the cell and line item selected within the cell generates a unique algorithmic attribute (4A.c1001.a.rB001.1L200.exd.t). This patient centric process provides a platform for adapting to the changing landscape of technology, Federal Mandates, Guidelines and Standards while generating e-audit trails. This harmonizing sequence of linking attributes between Actors, Objects, Functions and Infrastructure patient granted Access Control functions coupled with Privacy viewing, PII and PHI sharing privileges.

By way of further example, in case of an emergency a patient wants EMT's and Hospital Emergency Departments to have timely access both an Emergency Medical Data set and an Emergency Contact list. To achieve this goal, a consumer/patient who has been authenticated and has a Digital ID would consider providing consent on what specific information the consumer/patient wants shared with in the medical community defining specific events, titles and institutions as to what specific data is shared. In this scenario the consumer/patient starts with graphic of FIG. 4 (macro view) and FIG. 4A, a detailed view, which address how an individual engages the healthcare system in sharing emergency PHI and PII. The patient selects cell 1B line 2 which is 'EMT's' along with 3B line 2 (ER Medical Data Set) and 4G line 2 (Emergency Contacts) and in the process a unique algorithmic attribute is initiated.

A health care community/enterprise functions a separate yet parallel set standards and guidelines for engaging and sharing PHI. They too can gain access, in emergencies, access to critical health data and in some cases, operating federal guidelines, they can 'brake-the-glass' to access PHI without violating privacy laws. FIG. 5 (macro view) and FIG. 5A a detailed process on how medical professionals and EMT's gain access (using an enhanced standards based process) to access Emergency Medical Data Sets Emergency Contact information, if available. A Healthcare Community is represented by institutions, networks, system, clinics, etc. and is referred to as Objects in the standards world and is assigned attributes also. Medical professionals are defined as actors with authenticated identities (mandate) which incorporate their professional medical task and the entity they represent. In this scenario, presented by way of non-limiting example, an EMT selects the cell that defines the EMT's role as the EMT (1B line 2) along with information desired to perform their duties (emergency data and contact information): hence 3B line 2 is selected along with 4G line 2. This sets the infrastructure framework on what actors and their roles will be. Now protected health data is needed along with permission on how such should be shared.

Under HIPAA Privacy rules, the patient must provide consent as to what data they want to make available, to whom and under what conditions or events. By way of continued example, FIGS. 6 (macro view), 6A, 6B and 6C provide a sequential attribute process for enabling patient privacy consents in order to share confidential health information. This phase enables the sharing and viewing of PHI under patient defined events so the patient needs to be proactive in creating and selecting what information she or he wants shared from the health data repository. In the scenario, an EMT or ER physician/nurse must have a high degree of confidence in trusting the PHI being shared if it is to be used in clinical decision making. So a patient, using their digital ID, needs to create both an Emergency Data Set (FIG. 8) and or an Emergency Contact Set (FIG. 9) using their computerized Certified Personal Health Record and the subset Emergency Medical and Contact Dataset and electronically or digitally signing a record, making it available to EMT's and Hospital ER Departments. To provide the proper consent acknowledgments in sharing Emergency Data a patient would need to select/approve from FIG. 6A, Column C (share Emergency Medical & Contact Data), Row 1 (consent: Yes), Row 4 (acknowledge privacy rule), Row 6 (check Yes, permitting Restricted Data Sharing and Row 8 (Yes to Restricted Access). Since the patient generated their own Emergency Medical Data Set they must select and registered the type electronic device that was used to create their Emergency Data Set (such as their Personal Computer). This provides an end-to-end data integrity linkage with the accompanying attributes so Emergency medical professional can trust the integrity of PHI being shared.

Figure 6B:
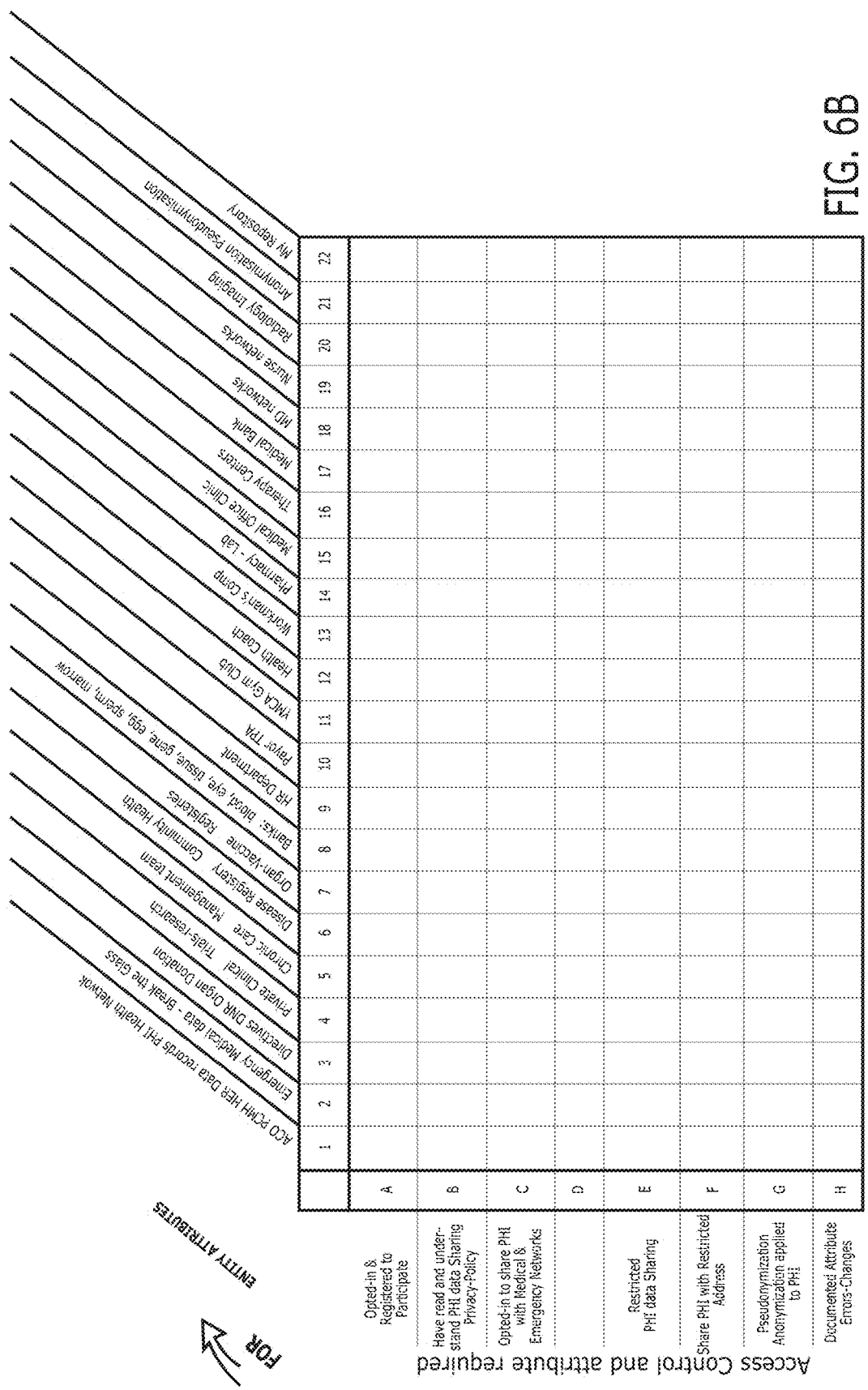
FIG. 6B illustrates parameters for sharing PHI and the entity attribute classes of Personal Health Information and defined location including by way of example, private and personal elected PHI data sharing attributes with health networks and groups including repositories, registers and designated entities.

FIG. 6B links the Patient to their professional medical network or hospital system where there is an infrastructure or framework in place for sharing electronic health information and where the patient has an established relationship, agreement or contract for coordinating care and sharing PHI, specifically Emergency Medical Data. In this scenario, in FIG. 6B, Column 2 (sharing Emergency Medical Data & Break the Glass) is selected and Row A (Opt-in & have Registered), Row B (accepted PHI data sharing policy), Row C (opted-in to sharing Emergency Data), Row D (elected Restricted Access to PHI), and Row E (elected Restricted PHI Data Sharing) are checked as is 1A Electronic Health Record data allowing EHR emergency to be shared with the patient's health network.

By way of non-limiting example, FIG. 6C defines what type of protected health data can be shared and with whom, by title and or name and in what time frame if there is a defined limit. In this scenario the FIG. 6C—A6 box is checked for EMT and Hospitals, ACO's PCMH's so emergency health data is shared with them and by checking A4 the same information will be shared with the patient's personal physician. (A medical directory of names would be provided). Additionally, the patient elects to have a copy of any Emergency Medical Record placed in their "Health Data Repository", Y1, so it too is current. The health data repository is a patient's personal health data secure file containing their PHI and electronic copies of the EHR documents that medical providers have shared with the patient.

By way of further example, FIG. 6A-6B illustrates a voluntary digital ID privacy attribute matrix relating FIGS. 6A, 6B and 6C that collectively interface with personal privacy selections for protecting health information, by way of example, associated with features, functions and access roles assigned as per FIGS. 4A and 4B and controlled by the patient, alternatively referred to as the actor or the user.

By way of yet further example, the above described system and methods are applicable to smartphone applications including a need for emergency medical data access. The teachings of the present invention also relate to such medical data access systems that operate under emergency conditions.

Consider, by way of example, that a user has an established authenticated ID received via a recognized and standards based identity proofing, verifying and validation process, as disclosed in U.S. Pat. No. 8,464,046 for Emergency Medical Data Access System and Associated Methods, and related pending U.S. Utility application Ser. No. 13/898,669 for Identity Validation System and Associated Methods filed on May 21, 2013, the disclosures of which are herein incorporated by reference in their entireties and commonly owned. In addition, consider that the user has elected, using their Authenticated ID, to populate the Emergency Medical and Contact DataSet, as described with reference to FIG. 10 that is provided with the identity proofing application.

One purpose for generating an Emergency Medical DataSet is that "in case of emergency" where the user is injured and or non-responsive, a user's Emergency Medical Information and or Emergency Contact Information (both with time-date stamped Consent's) are available for Emergency Department/EMT or Law Enforcement use. It is of interest to consider that State laws typically prohibit law enforcement from viewing a user's medical information. As a result, there are two separate and distinct presentations in a read only format, as described with reference to FIGS. 8 and 9.

The user generates the Emergency Medical and Contact DataSet using their own computerized database to populate the information and to securely post such to a secure site. By way of example, reference is made to FIG. 2C, items 146 for emergency data set access, 147 for emergency contact information, and 148 for organ donor status, and FIG. 3B for hospital search/Emergency Department). The Emergency DataSet application, when posted, automatically "designates authenticated access and privacy levels to sensitive data" as illustrated with reference again to FIG. 2C (wherein 143 for recognizing that all licensed medical providers, including EMT's, and law enforcement are required by law (Federal and State) to have authenticated digital ID's. When the user post's their Emergency Medical and Contact DataSet to a secure site (hosted by FEMA/DHS or NLETS/Police) it is accomplished through a certified 'Trusted Framework' as illustrated with reference to FIG. 3C (item 152).

By way of further explanation and example, and acknowledging a user can use a smartphone, for example, as their central user's mobile hub or possibly a laptop to generate their Emergency Medical and Contact DataSet, it is of interest to note that only the smartphone, is recognized by FCC, as a user registered mobile device can be used to provide access, "in-case of emergency or ICE", to "emergency contacts." Smartphones typically have an "emergency contact icon" reflected on the initial opening screen, or may be installed, when activated which does not require an access code when used (tapped). It directly generates an "in-case of emergency" (ICE) contact information form for the user to fill out or to provide a key pad for dialing 911. Law enforcement and EMTs make little use of searching a smartphone because data presented is not done so with a formal consent or with a time-date stamped authenticated signature or ID. Data cannot be trusted for clinical decision making.

By way of further example, secure sites and licensed professionals like FEMA/DHS, NLETS, local EMT's, law enforcement and medical professionals during untimely events can use their credentials to access ICE data at any geographical location nationally. ICE data must be consented to, time-date stamped and digitally signed.

With the teachings of the present invention, when an authenticated user (an authorized member, by way of example) integrates the defined serial number, make, model and cellphone number attributes of their smartphone and related registry data base recognizing the smartphone/mobile device as an extension of the user's authenticated attributes, the user can provide a piece of micro-code to the Telco as an ICE link to be used by EMTs, law enforcement and ER professional to access a user's personal Emergency Medical and Contact DataSet and/or have the smartphone provider provide an up link to the secure Emergency DataSet site such as NLETS and DHS/FEMA, by way of example.

A Blind Identity Trust Registry is herein referred to as a registry with Blinded Authenticated Identity Attributes that has a globally unique identifier that is assigned a unique user email address (P282, 14/60-64) with multifactor authentication functionality required that has an expiration date along with other authenticated personal attributes. P282, 0065 the trusted process validates the user's ID and provides an authentication process. Given: It is recognized that when a RP questions or makes a request for additional attribute information, the RP always corresponds with the user's Identity Proofing agent-IdP. There are selected individuals who want to remain Anonymous and that all transactions be doubled blinded so that the IdP and the RP remain blinded from the other. For a user to want to become Anonymous they first must be known, credentialed, authenticated with a high level of trust. As earlier noted, Anonymization and Pseudonymization are specific de-identification processes that file the intent of HIPAA 1996 and the HIPAA omnibus rules of January 2013.

An authenticated user, who is credentialed and has high Trust Level status, such as a sports figure, executive, celebrity or Politian and wants to have an anonymized authenticated identity, must follow an anonymity identity process if offered by an IdP. Pseudonymization is a specialized class of Anonymization that removes the association and adds an association between a particular set of data characteristics relating to the data subject in addition to adding more pseudonyms. This is a means by which information can be linked together to the same group of persons over time and across multiple data records without revealing the identity of the person and subject data. A trusted third party play's a critical role if there needs to be a re-identification event that is in response to a major public health event all of which is defined in HIPAA.

The doubled blinded process is initiated when the user makes a request to their IdP using their authenticated Identity on their authenticated device that is bound to their digital identity while also providing a 'chosen name' and an executed consent form for creating a double blinded trust identity Registry Account. The IdP, in a separate, secure and confidential process, coordinates with a Blind Trust identity Registry service or trust entity, and ask them to set up a B double blinded Authenticated Identity Attribute Account (encrypted) that will allow it to recognized credentials from a designated globally unique identifier coupled with multifactor authentifies, including a minimum of two biometrics one being voice and a unique secure email address. The Blind Trust ID Registry will also create a unique user Trust ID code along with supporting Bar or QR tag codes associated with biometrics used, including tokens, which are used to communicate with the user's IdP and the Authenticated User. The Blind Trust ID Registry supporting components may elect to have a PKI or a partial non-public PKI used depending on the auditing platform. When finalized and approved, the IdP will bind the Blind Anonymity credential to the user's authenticated Identity with a digital signature and log it in secure blind trust identity registry that requires partial non-public or full strength PKI.

It will generally be of interest to note that one focus of the present invention is to place users in control of managing their identity and providing consent when interacting using the Internet. For a digital identity to be functional, it must be applicable in environments where a user elects to use it to be identified. Once an identity has been fully verified and validated and is authenticated, it may be converted to a digital format in various forms using identity technologies and digital signing forms which build on each other's strength. No specific technology is singled out, only that an authenticated identity will be assigned some form of a digital certificate structured profile coupled with authenticated attributes. It must coexist with and complement existing authentication systems. In other words, it must be technology independent.

It may be helpful to again address use of the terms "verification" and "validation" which are independent procedures used together for checking to see that a product, service or system meets requirements, specifications and fulfill an intended propose. Given, by way of example, that a candidate provides subjective identity data for consideration. Verification is a process that checks to determine the authenticity of the asserted identity data. Validation is intended to confirm that the identity asserted matches and meets the initial attributes of the original identity and related specifications requirements such images, demographics, prints, nomenclatures and regulations. In order to strengthen the foregoing and maintain a high level of confidence in data generated and integrity in the electronic data sharing process such as in healthcare by way of example, the process must incorporate e-audit trails, have a traceable electronic enterprise infrastructure and generate key bench mark performance indicators.

By way of example, while Dettinger, Schaufele, and Moshir may seek to validate a resident address via the government postal service, check a state driver's license registration, a passport registration or a bank card number in order to match one piece of data to another, there is not a verifiable and true validation to a high level of confidence as to the person being who he or she claims to be. Scott T Kimmel, Biometric Technologies, Inc., the 'Event Storage' states that one needs to obtain a biometric signature and patient ID and such an event creates the foundation for generating a patient record. Yet, if the ID is stolen, then one is making an assumption that when a patient is registering that the biometric signature and the Patient ID represent is an authenticated and validated ID set of attributes for that patient, thus remaking a false assumption.

Further, many states do not reciprocate and recognize another state's driver license or have ready access to passports which are under Federal control and thus lack the ability to access and check the authenticity of a passport document. State and national ID cards, financial credit/debit cards have marginal impact in verifying an identity. Biometrics data have a strong impact in the verification process when integrated with other forms of identity attributes and authenticated attributes. A biometric image captured by a government agency or a certified trusted $3^{rd}$ party, an independent party, recognized as a credentialed source is one step in fully vetting ones identity which includes verifying and validating all or as many as possible attributes of an identity. Dettinger, Schaufele and Moshir each, individually and collectively, state they would use some form of authentication (i.e. checking a driver's license) or security method (PKI) to help provide data security and access control. If they generate the "private key" for their institution, it is self-serving for their institution thus not universal and portable as is being set forth. The three cited patent references also state they would also consider validating a digital signature which must first be vetted and established as a trusted ID attribute. Yet, in each of the three cases there is no stated recognition that the digital signature they would use would be verified independently. Hence, it would be for internal use only and not for securely sharing confidential information in a distributed enterprise. As set forth in the claimed invention, authenticity of the client/patient and verifying and validating who they are electronically generates an electronic credential, the electronic security certificate that operates via a trusted service platform.

The Trust Service Platform is a user's digital portal and gatekeeper, a dynamic and stable layer of software, registries, policies and rules engines that harmonizes and synthesizes user's data, based on their consent, to aide in identity management, access control, delegation of authority and sharing protected information. The secure digital Platform monitors a user's identity attributes and smart device hub along with connected devices, applications, sensors, things and defined relationships integrated with privacy and security auditing and compliance functions. The foundation for the Platform incorporates Identity proofing, identity access management and relying party gatekeeping functions that are the building blocks for supporting, protecting and governing the user controlled health and personal data trust repository that hosts a user's personal identifiable information and protected health information.

Yet further, the references cited use of ID validating techniques within each of their closed "cloud computing" enterprises to verify their clients or customers, but the ability to transport their 'intra verifiable identities' from their closed "cloud" computing system is limited if not restricted. By way of example in the world of health data automation, the process of clinical data capture and secure electronic data/file sharing of patients protected information is a centerpiece in the health exchange infrastructure. The secure data exchange process only becomes a reality when each participant can be electronically identified and that occurs once their personal attributes have been fully verified and validated as to who they say they are with a high level of assurance. The claimed invention provides such a solution.

Figure 11:
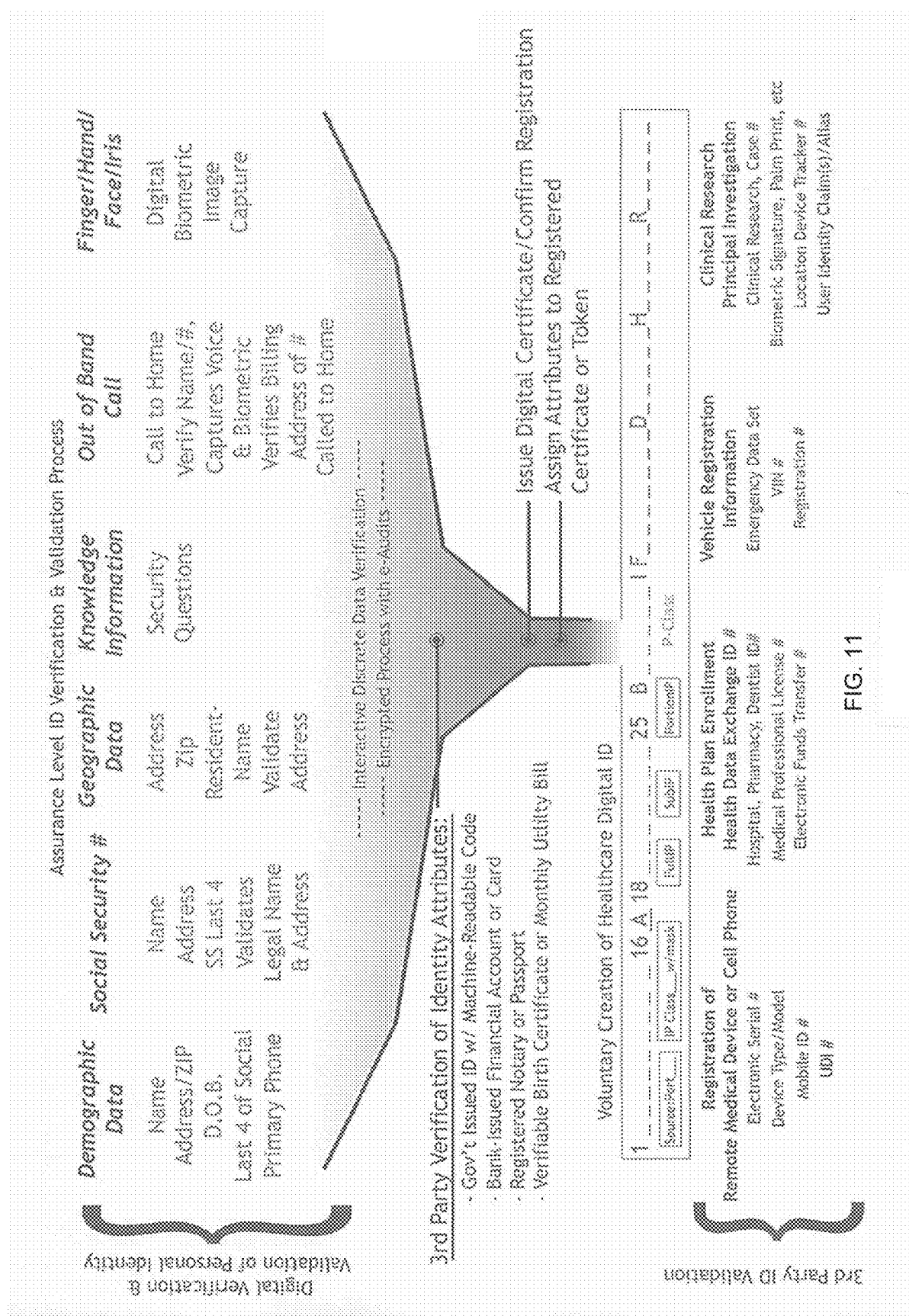
FIG. 11 is a flowchart diagrammatically illustrating the identity authentication process that may be adapted to any industry once a person is authenticated and has a digital ID.

It may also be helpful to further illustrate the assurance level identification and validation process with reference again to the flow chart of FIG. 11, by way of example, including a healthcare theme as an example for this industry has a critical identity problem. But it is important to note that the identity authentication process can be adapted to any industry for once one is authenticated and has a digital ID they can use various attributes they assign to their name/digital ID they can adopt the feature/attribute they can use it to control their identity when they interact with a specific venue on the internet. Healthcare would most likely use a Voluntary/Universal ID type standards base model for identity verification while other industries would elect a different form or path such as a digital ID on a user smartphone plus a biometric signature or voice combination (multifactor authentication) that would be a site-to-user form of digital ID verification established by the business site and their customers. It is important to note that the user is in control of his identity attributes when engaging the internet.

The flow chart of FIG. 11 runs from top to bottom and is divided into three sections with the top section including an initial phase (Digital Verification & Validation of Personal Identity) where one would have their name verified and validated using six or seven attributes of the individual in order to establish a level of assurance or Trust as to who that person electronically says they are, creating an authenticated attribute. By way of example, if an assurance or trust level is in question for the individual, then they are a candidate for further vetting or the individual may wish to achieve a higher confidence and assurance level for a trusted Identity. If such is the case, one may elect to use a 3rd Party Verification of Identity Attribute, as illustrated in the flow chart (left-center side of flow chart). Once a person's ID has been authenticated, then a Voluntary Creation of Healthcare ID is generated (with consent); one ID is for external market use while the second ID is for internal use specifically for identity and access management, privacy control and for securely defining and designating what PII (Protected Identifiable Information) and PHI (Protected Health Information) is to be shared and under what conditions.

By way of further example as to how a business may use an authenticated biometric (e.g. Identity) attribute to conduct a secure transaction, consider a legally registered company with a verifiable tax ID number, address, and telephone number. Such a company may host a web site for conducting secure transactions with customers and specify that one or several authenticated biometric attributes, that have been previously verified and validated, be used to conduct and process business transactions. The ID designation includes a number that is globally unique and includes a check digit process for validating the number generated through a standards process, and then expanded to include a unique Privacy Class so that private identifiers are anonymous. This provides a desirable function and distinguishing feature for a patient. For example, if one elects to add a device, a plan or other enhancing function, they must engage a third party validation process to first register the medical device or cell-smartphone, or enroll in a health plan before such can be incorporated with their Authenticated Identity. While this process may be used when we buy a cell phone, enroll in a health plan, buy a car or engage in a research project, this activity validates the identity which has already been fully vetted (V&V).

It may be helpful to better understand the personal dataset and allowing access to at least one person other than the user by considering a Voluntary ID, by way of example as with continued reference to FIG. 11 to include four alpha-numeric categories F (families), D (an electronic Device), H (health plan), R (research or the addition of other validated devices/features) each has numeric place holders. One purpose is to voluntarily extend one's identity to any one or a combination of a family, a medical device, a health plan, a vehicle to an organ donation plan or to a research program or the addition of a new function associated with one's identity. This process provides portability of one's authenticated identity in an automated enterprise where sharing sensitive information is critical and security is mandated.

In contrast to known practices, the invention teaches completing substantive validation and registration process and reinforces the uniqueness in on-line identity proofing and an attribute authentication process. Once a person has been authenticated with a credentialed identity, the teachings of the present invention fine tune an email feature, by way of example, with additional authenticated micro object attribute features, such as presented with an electronic time-date stamped post mark which is an embedded email-authenticated object attribute, issued by the United States Post Office, by way of example. A second attribute feature reinforces the validation of a user's demographic information using an "elink authentication" process by creating a unique email address incorporating USPS.Gov as text along with the user's address, by way of further example.

Understanding terminology used by those skilled in the art will be helpful in further understanding the distinction between the claimed invention and the teachings of the cited patent references. To reiterate the above described, a person's identity has a unique authenticated identity credential with authenticated relevant personal attributes collected and recorded into the system. The individual/person is also recognized as a Subject or user and she/he can be assigned one or more attributes and object attributes. As above described, attributes are characteristics of a subject, object or environmental condition. Attributes contain information that defines a personal identity or a name-value pair to an object. An attribute is an inherent bit of data or characteristic that can be authenticated or validated. Attributes are the key features to privacy and user access control functions. An Object Identity is a data resource that is managed by an Attribute Based Access Control system an integral part of the Trusted Service Platform that integrates data types or groups, devices, files, records, services, tables, process, programs, applications, networks, or domains containing or receiving information. Objects are defined relationships by descriptive definitions and attributes bound to authenticated identity credentials and pre-defined operational events and environmental conditions. An Event or Environmental Condition is an independent conditionally identified event or condition that is attribute identified that can be bound to a subject or objects identity and may include a current time, a day, a temperature, day-of-week, location-of-user (GPS) or an emergency event. Upon a previously defined condition or event occurring, then an Operational event will occur.

A goal of an electronic identity verification and validation process is to establish the trustworthiness of an authenticated electronic identity (eID) so that when an attribute(s) of the validated eID are presented they provide a level of confidence as to who you are electronically as a genuine person and that of an impostor. One's e-identity is a composite of verifiable evidence from that person's unique human and social elements that make up their identity. It is this uniqueness of personal attributes, features, historic actions and data elements, which when verified and validated formulate a repository of trusted attributes that generate an authenticated eID. An eID is a sensitive combination of personal attributes derived from a corroboration of evidence of one's identity comprised of unique personal elements and characteristics integrated with trustworthy personal documents that can be third party verifiable and validated. The establishment of a person's unique identity is comprised of personal identity attributes that represent: Something you are: (core and unique identifiers, a biometric, tattoo); Something you have: (birth certificate, driver's license, government issued ID/Passport, a financial account); and Something you know: (personal historic knowledge). The combination of evidence is a collection of elements with different levels of trustworthiness and authenticity. Each attribute must be validated in person, remotely via document validation signature or electronically or through a trusted third party/issuer of record with the source of such information being weighted. The combination of weighted positives and contra-indications provides a bench mark for a level of assurance in creating an authenticated eID.

Considering the advancement in smartphone technology, various government agencies are exploring the idea of mobile driver licenses and internet passports which, in their paper form, are universally recognized as high-assurance, government issued, credential documents, a core feature in the identity proofing process to authenticate a user, as illustrated with reference to FIG. 7A. If these documents were in a digitally certified electronic format that could be stored as a personal asset on a user's smartphone, how could a user strengthen or authenticate their identity, real-time, on-line with little friction or effort?

Consider, for example, a user who has a low level, basic vetted self-asserted social identity (Facebook, Google, Yahoo or LinkedIn) that requires a user name and password and who also has the standard third party authenticated credential on their person (driver's license, passport, green card and or EMV payment card). How would the 'before and after' digital automation of credential documents benefit a user?

In the current form, to enhance or up-grade a user's flexibility in applying their validated high assurance credential to a transaction, assuming the user has already been vetted, the user must provide images of the credential that reflect the chip, bar or QR code, its number expiration date with the user's name; all to be verified and validated before being posted in the user's Authenticated Attribute Registry. As a follow up process, the authenticated document attributes must then be bound to the user's authenticated identity and device. The process is detailed for audit purposes, not real time and not a one-time process.

Now consider the same credential documents being issued in a digital mobile or internet format specifically designed for smartphones that a user already has in their smartphone device. When a user elects to elevate the strength of their identity for a specific transaction or to address a Relying Party issue, the user only needs to present the digital image of the credentialed document on their user-hub smartphone that is authenticated to the user. The digital image will reflect the document, its chip, bar code or QR code that will be read electronically while being displayed while also enabling real time verification of the document's visual security features by the issuing third party authority. During a virtual exchange, the user may also be asked, by way of example, to take a real time selfie facial photo on their smartphone to send to the verifying party so they can check the facial image against the original photo capture by the document provider. This real time process can provide the user with a three-factor authenticated digital identity credential that can be trusted and reused; the authentication process would not have to be repeated until the credential expires.

Important authenticating and validating building blocks in this high-assurance, internet credentialing process originates with the government agencies that provide the authenticated documents: Department of Transportation/State DMV's, State Department or the Federal Reserve that regulates banks that issue EMV payment cards. Financial institutions are required to perform a "know your customer" verification process before allowing a customer to open a bank account including an EMV payment card account. And when the user's EMV card is inputted-enrolled on a user's primary smartphone device, it is fully empowered and ready to use and for security reasons it must be coupled to a secure message process such as secure email that serves as a security buffer.

It is important to note that no one class of attributes can provide a high level of trustworthiness to create an eID. But once a unique e-identity is created, a validated attribute of that person can be used as trusted pointer/key to person's authenticated eID. An identity verification process does not convey or grant a value, benefit or privilege. It is an electronic instrument to provide a level of authenticity and confidence as to one's eID and related trusted attributes. An authenticated eID must carry with it a high level of trust and assurance in order to maintain trust and integrity in the eID process and to continually challenge the system to single out identities of questionable character.

A trusted identity management process incorporates critical components and national standards that generate authenticated eID's that can be trusted with a high level of assurance. The system architecture is designed around a trusted exchange of related third or independent parties focused Personal Privacy in controlling the use of one's electronic identity (eID), Security, Confidentiality, Accountability, Traceability and Integrity. Electronic audit trails and traceability are key features that provides e-trails and electronic date stamps for measuring results and addressing claims made by others or who provided access for verification and validation activities as a trusted party or regulatory authority.

To reemphasize problems solved by embodiments of the present invention, it is again helpful to use the healthcare industry as an example. The healthcare industry, like many industries, is transitioning from a paper based system to an automated enterprise infrastructure that is electronically distributed in the medical community where personal health information and sensitive confidential data is captured electronically and securely shared. Currently licensed medical provider's (doctors, nurses, pharmacists, EMT's, etc.) who diagnose, provide care and prescribe are in the early to mid-phase in the automation process of capturing and exchanging clinical data. In late 2013, under the federal plan, patients will be incorporated into the mix, by their medical provider, empowering patients to take a more active part in managing their health activities. Patients will be engaged electronically by receiving email-reminders, text messages referencing a medical test, educational health tips and be encouraged to record and send a medical value electronically (blood pressure, blood sugar, weight, did you take medication, how do you feel today, and the like.) to their provider via their cell phone, computer or other approved medical device. The sharing of medical data is in part protected under HIPAA legislation, but does not proactively offer an umbrella of protection in a litigious and fraudulent market place where identity theft and medical identity theft is on the increase. Hence a medical provider must have a high level of trust and assurance that the integrity of medical values provided by a patient electronically is in fact from that patient, before such data can be incorporated into a clinical decision process.

Further, it will be understood by those of skill in the art that flowcharts and block diagrams herein described may illustrate architecture, functionality, and operation of possible implementations of systems, methods and computer program products according to various embodiments. Therefore, it will be understood that each block in the flowchart or block diagram may represent a module, segment, or portion of code, which comprises one or more executable computer program instructions for implementing the specified logical function or functions. Further, some implementations may include the functions in the blocks occurring out of the order as herein presented. By way of non-limiting example, two blocks shown in succession may be executed substantially concurrently, or the blocks may at times be executed in the reverse order, depending upon the functionality involved. It will also be noted that each block of the block diagrams and flowcharts, and combinations of blocks in the block diagram and flowchart illustrations, may be implemented by special purpose hardware-based systems that perform the specified functions or acts, or combinations of special purpose hardware and computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram. These computer program instructions may also be stored in a computer readable medium that may direct a computer, other programmable data processing apparatus, or other devices to function in a particular manner, such that the instructions stored in the computer readable medium produce an article of manufacture including instructions which implement the function or act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Aspects of various embodiments as herein presented, by way of example, may be embodied as a system, method or computer program product, and accordingly may take the form of a hardware embodiment, a software embodiment (including firmware, resident software, micro-code, and the like) or a combination thereof that may generally be referred to as a circuit, module or system. Furthermore, aspects of various embodiments may take the form of a computer program product embodied in one or more computer readable media having computer readable program code embodied thereon.

It is also understood that a computer implemented method as may herein be described operates with readable media relating to non-transitory media, wherein the non-transitory computer-readable media comprise all computer-readable media, with the sole exception being a transitory, propagating signal.

Any combination of one or more computer readable media may be utilized. A computer readable medium may be a computer readable signal medium or a computer readable storage medium. A computer readable storage medium may be, by way of non-limiting example, an electronic, magnetic, optical, electromagnetic, infrared, or semiconductor system, apparatus, or device, or any suitable combination of the foregoing. More specific non-limiting examples of the computer readable storage medium may include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that may contain, or store a program for use by or in connection with an instruction execution system, apparatus, or device.

A computer readable signal medium may include a propagated data signal with computer readable program code embodied therein, by way of non-limiting example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that may communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, NFC and the like, or any suitable combination thereof. Computer program code for carrying out operations for aspects of various embodiments may be written in any combination of one or more programming languages, including an object oriented programming language such as Java, Smalltalk, C++ or the like and conventional procedural programming languages, such as the C programming language or similar programming languages. The program code may also be written in a specialized language such as for a smartphone. The program code may execute entirely on the user's computer or smartphone, partly on the user's computer, as a stand-alone software package, partly on the user's computer and partly on a remote computer, or entirely on the remote computer or server. The remote computer may be connected to the user's computer through any type of network, including a local area network (LAN) or a wide area network (WAN), or the connection may be made to an external computer, by way of non-limiting example, through the Internet using an Internet Service Provider.

Having now described the invention, the construction, the operation and use of preferred embodiments thereof, and the advantageous new and useful results obtained thereby, the new and useful constructions, and reasonable equivalents thereof obvious to those skilled in the art, are set forth in the appended claims.

That which is claimed is:

1. A computer implemented method for personalizing a secure personal database using a hub device, the method comprising:
   electronically receiving a personal dataset including identifiable attributes of a user by a hardware processor;
   electronically verifying authenticity of an asserted identity of the user including the identifiable attributes;
   electronically verifying the personal dataset;
   storing the personal dataset on the secure personal database;
   validating the identifiable attributes of the user, wherein the validating includes confirming the asserted identity matches the identifiable attributes;
   generating a digital security element as a result of the verifying and the validating of the identifiable attributes;
   enabling the digital security element for granting electronic access to the personal dataset on the secure personal database by an authorized member of an authorized registry;
   designating privacy levels of trust for access to the personal dataset by the user, wherein the levels of trust are limited by data use directives;
   authorizing the access to the personal dataset by the user for the authorized member based on at least one level of trust; and
   activating a hub device application by the authorized member for accessing the secure personal database through the identifiable attributes.

* * * * *